(12) United States Patent
Andersen et al.

(10) Patent No.: US 6,610,516 B1
(45) Date of Patent: *Aug. 26, 2003

(54) CELL CULTURE PROCESS

(75) Inventors: Dana C. Andersen, Redwood City, CA (US); Tiffany M. Bridges, Burlingame, CA (US); Martin Gawlitzek, Foster City, CA (US); Cynthia A. Hoy, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/723,545

(22) Filed: Nov. 27, 2000

Related U.S. Application Data

(62) Division of application No. 09/553,924, filed on Apr. 21, 2000.
(60) Provisional application No. 60/131,076, filed on Apr. 26, 1999.

(51) Int. Cl.[7] .......................... C12P 21/04; C12P 21/06; C12N 1/20; C12N 5/06; C07K 1/00

(52) U.S. Cl. .................. 435/70.1; 435/69.1; 435/252.3; 435/358; 530/395

(58) Field of Search .......................... 530/395; 435/69.1, 435/69.6, 252.3, 358, 359, 70.1

(56) References Cited

U.S. PATENT DOCUMENTS

| | | | |
|---|---|---|---|
| 4,560,655 A | 12/1985 | Baker | |
| 4,657,866 A | 4/1987 | Kumar | |
| 4,752,603 A | 6/1988 | Collen et al. | |
| 4,766,075 A | 8/1988 | Goeddel et al. | |
| 4,767,704 A | 8/1988 | Cleveland et al. | |
| 4,927,762 A | 5/1990 | Darfler | |
| 5,122,469 A | 6/1992 | Mather et al. | |
| 5,705,364 A | 1/1998 | Etcheverry et al. | |
| 5,721,121 A | 2/1998 | Etcheverry et al. | |

OTHER PUBLICATIONS

Parekh et al. Cell–Type–Specific and Site–Specific N–Glycosylation of Type I and Type II Human Tissue Plasminogen Activator, Biochemistry, 1989, vol. 28, No. 19, pp 7644–7662.*

U.S. patent application Ser. No. 09/470,849, Etcheverry et al., filed Jun. 6, 1995.

U.S. patent application Ser. No. 09/705,285, Etcheverry et al., filed Jan. 11, 2000.

U.S. patent application Ser. No. 09/723,625, Andersen et al., Nov. 27, 2000.

Mather, Jennie P. *Mammalian Cell Culture, the Use of Serum–Free Hormone–Supplemented Media*, Plenum Press, New York pps. vii–x, 1–15, 17–52, 129–150 (1984).

Rudinger, J., "Characteristics of the Amino Acids as Components of a Peptide Hormone Sequence" *Peptide Hormones*, J.A. Parsons, Baltimore:University Park Press pps. 6 (1976).

Wilhelm, J., et al., "Alterations in the Domain Structure of Tissue–Type Plasminogen Activator Change the Nature of Asparagine Glycosylation" *Bio/Technology* 8:321–324 (Apr. 1990).

Castro et al., "The macroheterogeneity of recombinant human interferon–gamma produced by Chinese–hamster ovary cells is affected by the protein and lipid content of the culture medium" *Biotechnology and Applied Biochemistry* (abstract only) 21(1):87–100 (1995).

Castro, P. et al., "The macroheterogeneity of recombinant human interferon–gamme produced by the Chinese–hamster ovary cells is affected by the protein and lipid content of the culture medium" *Biotechnology and Applied Biochemistry* 21(1):87–100 (1995).

Gebert and Gray, "Expression of FSH in CHO Cells. II. Stimulation of hFSH expression levels by defined medium supplements." *Cytotechnology* (abtract only) 17:13–19 (1995).

Gebert, C.A. and Gray, P.P., "Expression of FSH in CHO cells. II. Stimulation of hFSH expression levels by defined medium supplements" *Cytotechnology* 17:13–19 (1995).

Hosoi et al., "Modulation of oligosaccharide structure of a pro–urokinase derivative (pro–UKΔGS1) by changing culture conditions of a lymphoblastoid cell line Namalwa KJM–1 adapted to serum–free medium" *Cytotechnology* 19:125–135 (1996).

Kimura and Miller, "Glycosylation of CHO–derived recombinant tPA produced under elevated pCO–c" *Biotechnology Progress* (abstract only) 13(3):311–317 (1997).

Kimura, R. and Miller, W., "Glycosylation of CHO–derived recombinant tPA produced under elevated pCO–2" *Biotechnology Progress* 13(3):311–317 (1997).

Lamotte et al., "Na–butyrate increases the production and alpha2, 6–sialylation of recombinant interferon–gamma expressed by alpha2, 6–sialyltransferase engineered CHO cells" *Cytotechnology* (abstract only) 29:55–64 (1999).

(List continued on next page.)

Primary Examiner—Karen Cochrane Carlson
Assistant Examiner—Rita Mitra
(74) Attorney, Agent, or Firm—Janet E. Hasak

(57) ABSTRACT

A glycoprotein is produced by a process comprising culturing mammalian host cells expressing nucleic acid encoding a glycoprotein in the presence of (a) a factor that modifies growth state in a cell culture, (b) a divalent metal cation that can adopt and prefers an octahedral coordination geometry, and/or (c) a plasma component. In this process, the occupancy of an N-linked glycosylation site occupied only in a fraction of a glycoprotein is enhanced. Such culturing is preferably carried out at a temperature of between about 30° C. and 35° C. and/or in the presence of up to about 2 mM of a butyrate salt and/or in the presence of a cell-cycle inhibitor.

1 Claim, 8 Drawing Sheets

OTHER PUBLICATIONS

Lamotte, D. et al., "Na–butyrate increases the production and alpha2, 6–sialylation of recombinant interferon–gamma expressed by alpha2, 6–sialyltransferase engineered CHO cells" *Cytotechnology* 29:55–64 (1999).

Madoiwa, S. et al., "Effect of carbohydrate side chain of tissue–type plasminogen activator on its interaction with plasminogen activator inhibitor–1" *Fibrinolysis & Proteolysis* 12(1):17–22 (1998).

Nabi and Dennis, "The extent of polylactosamine glycosylation of MDCK LAMP–2 is determined by its Golgi residence time" *Glycobiology* 8(9):947–953 (1998).

West and Brownstein, "EDTA treatment alters protein glycosylation in the cellular slime mold dictyostelium–discoideum" *Experimental Cell Research* (abstract only) 175:26–36 (1988).

West, C.M. and Brownstein, S.A., "EDTA Treatment alters protein glycosylation in the cellular slime mold dictyostelium–discoideum" *Experimental Cell Research* 175:26–36 (1988).

Woodfork, K. et al., "Inhibition of ATP–sensitive potassium channels causes reversible cell–cycle arrest of human breast cancer cells in tissue culture" *Journal of Cellular Physiology* 162(2):163–171 (1995).

* cited by examiner

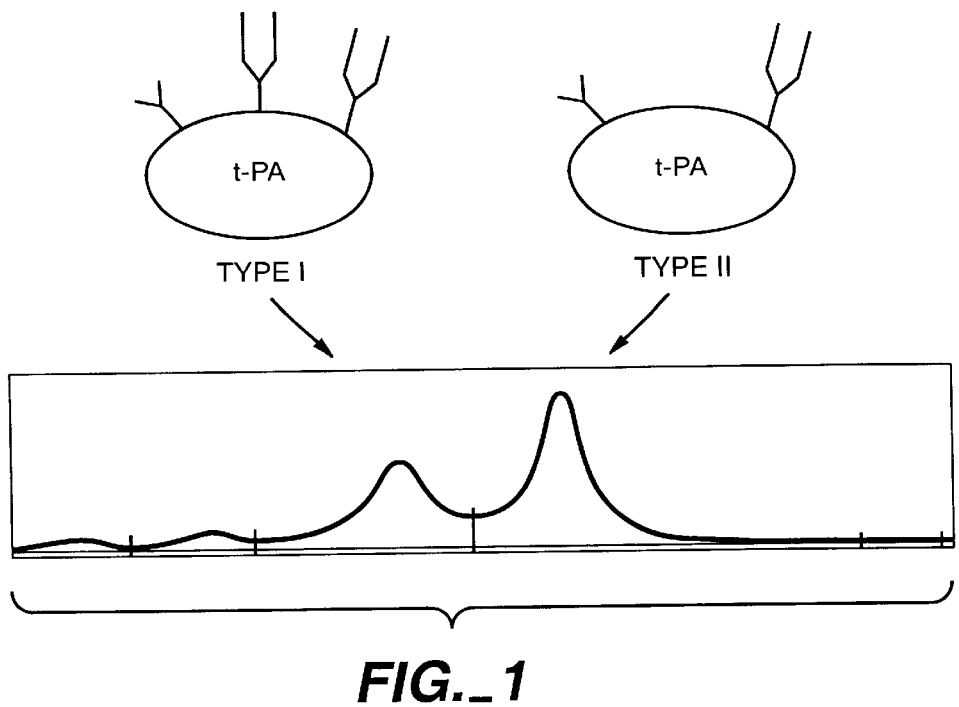
FIG._1
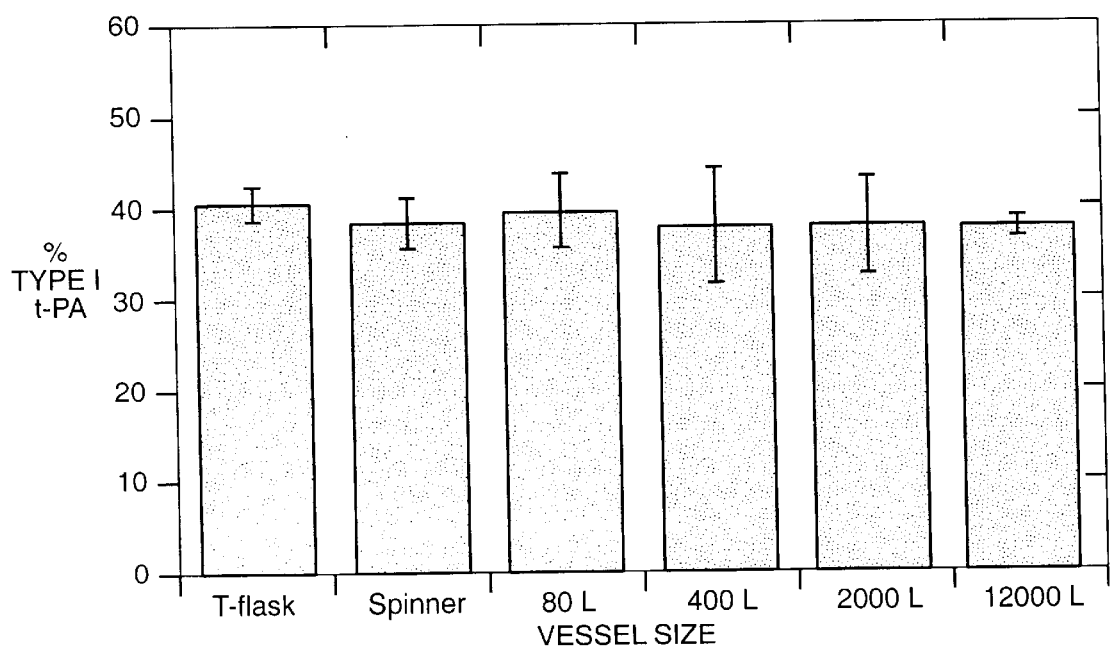
FIG._2

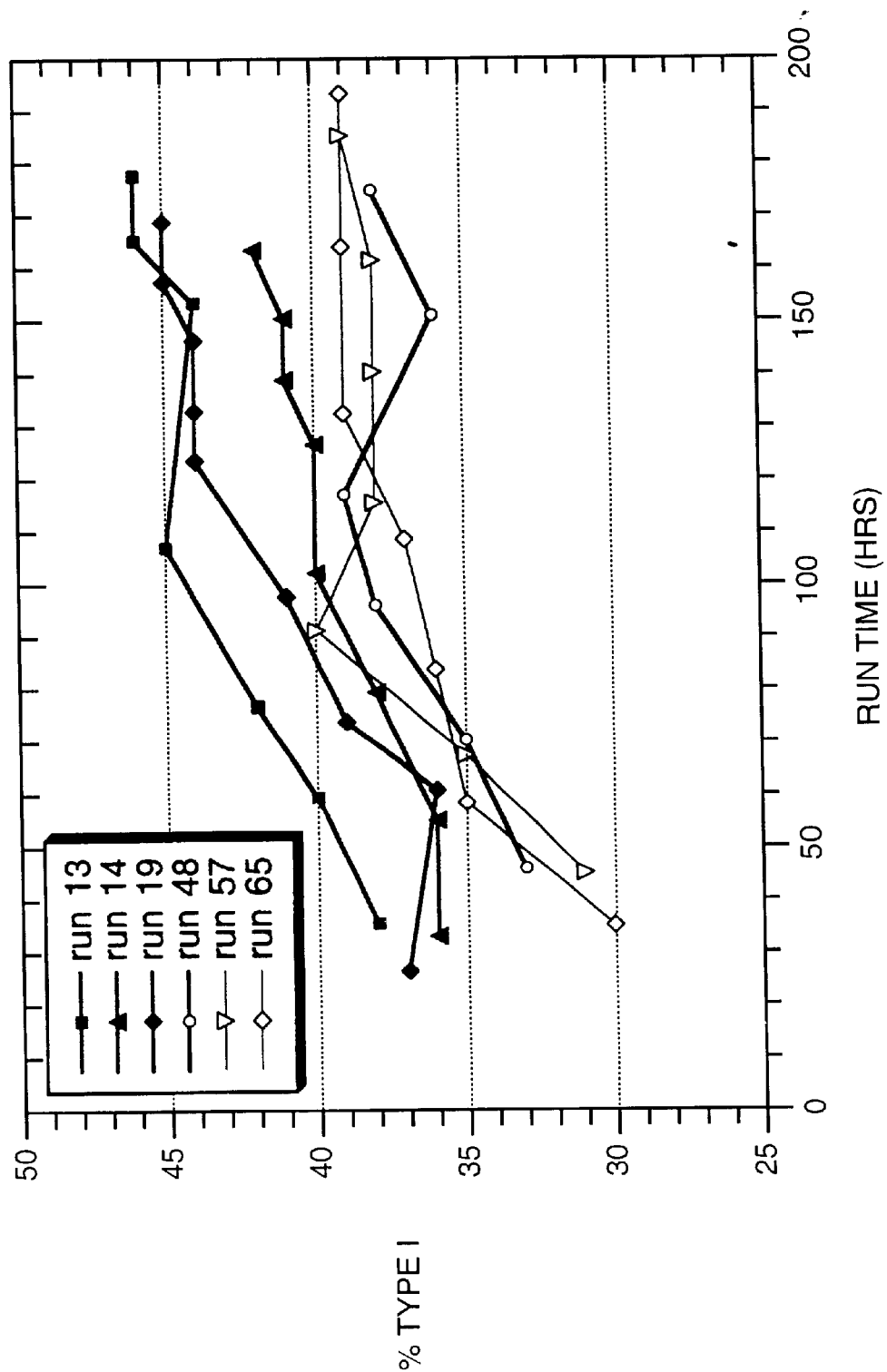
FIG._3

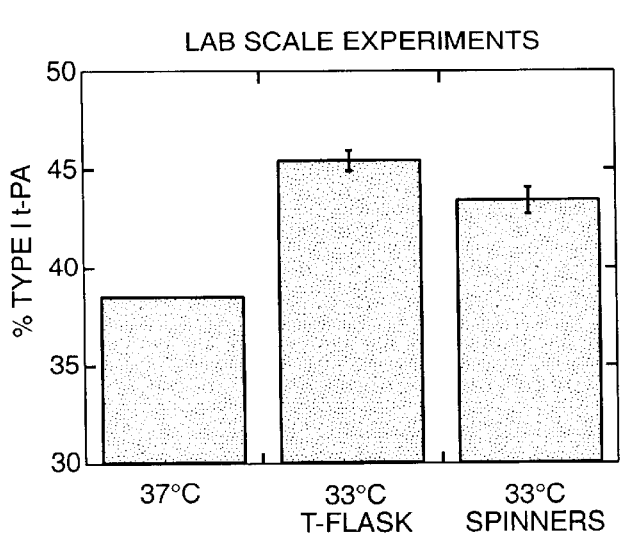
FIG._4A
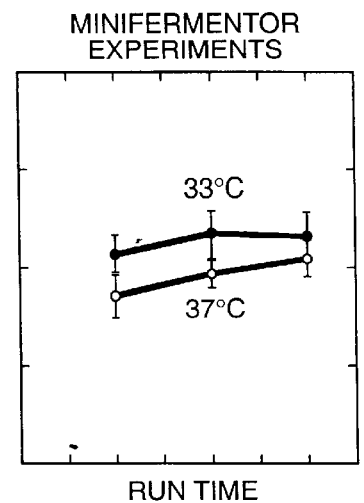
FIG._4B
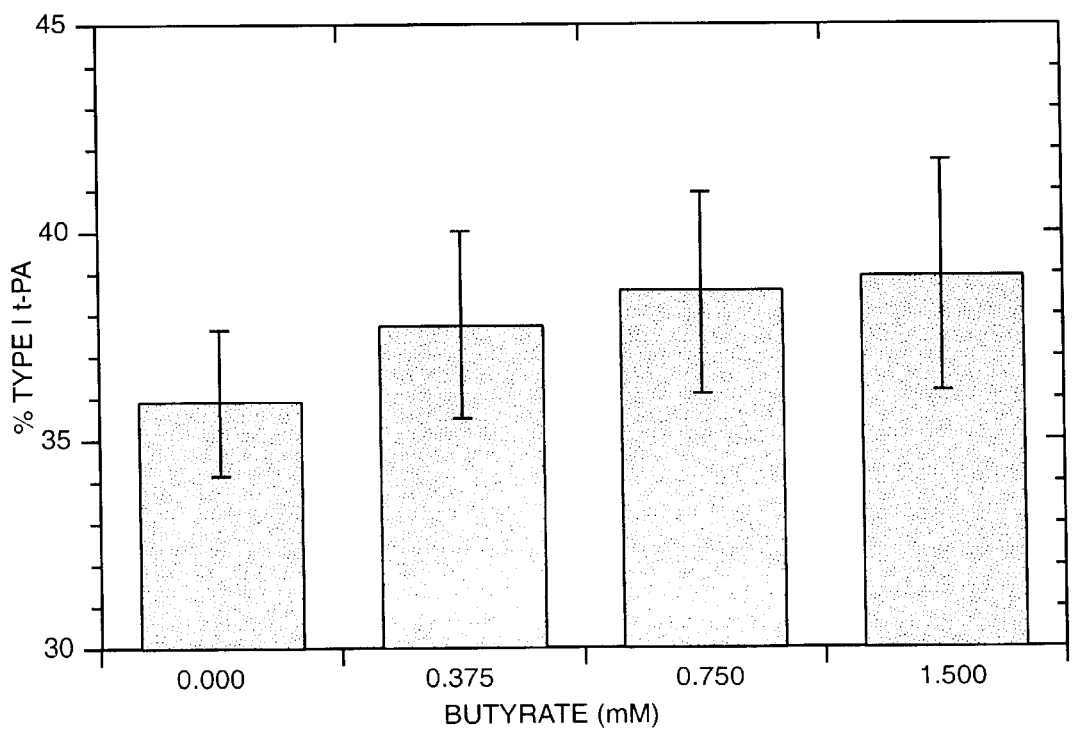
FIG._5

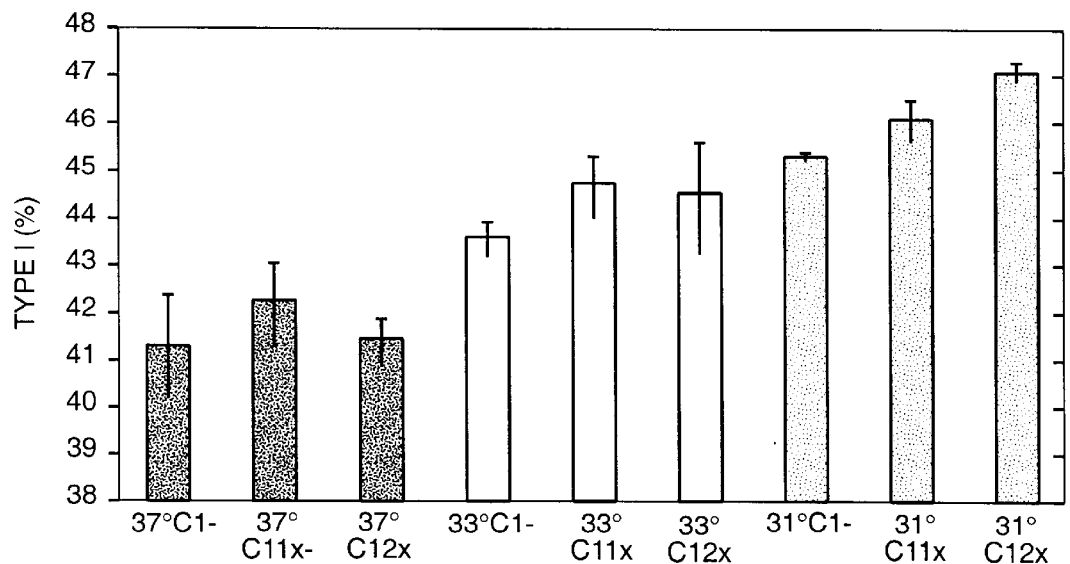
FIG._6
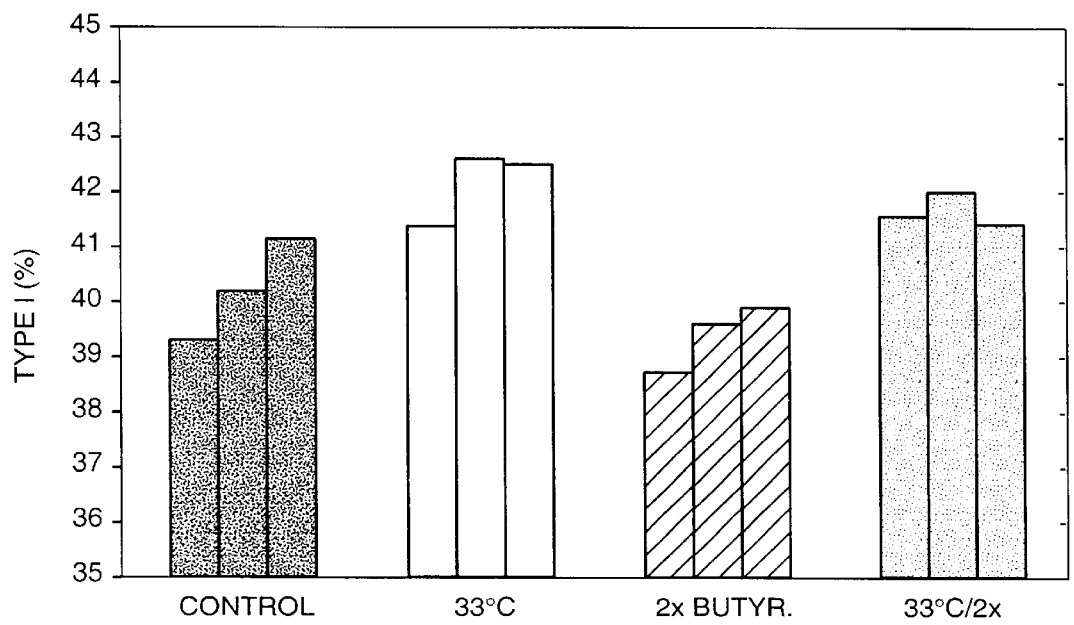
FIG._7

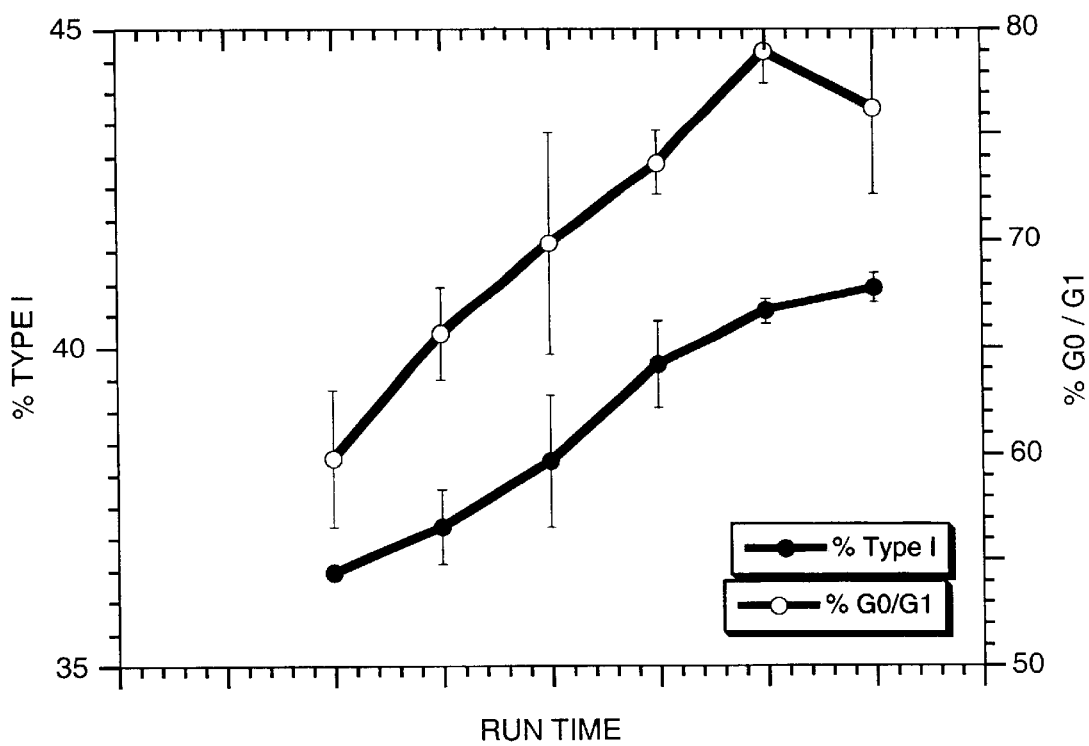
FIG._8
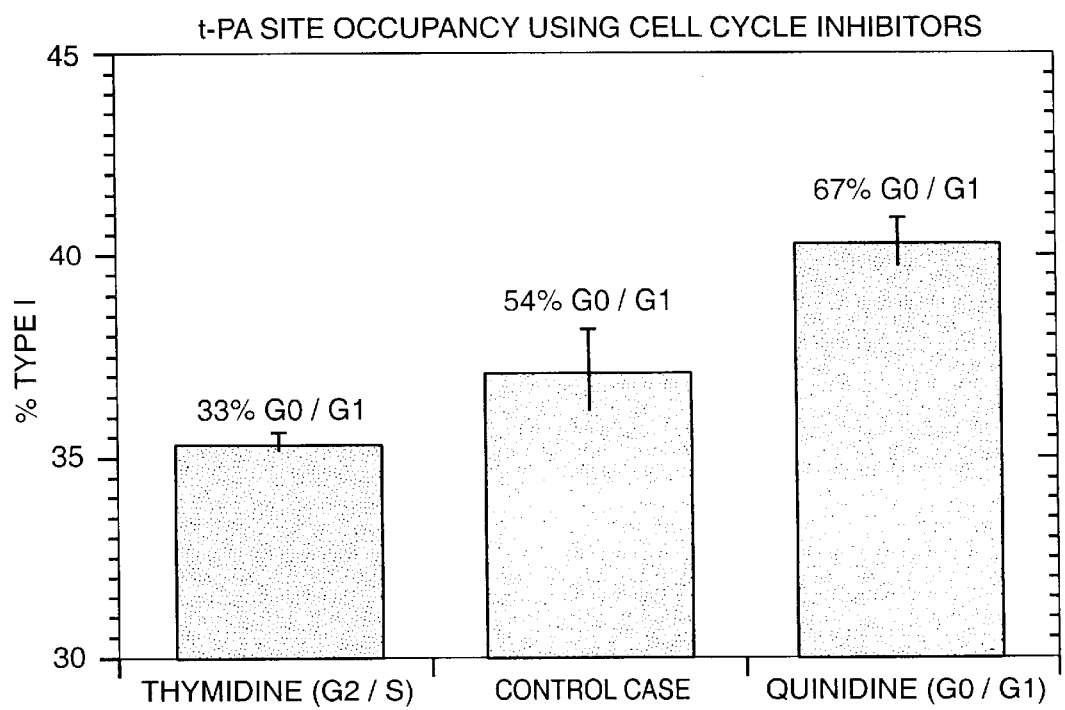
FIG._9

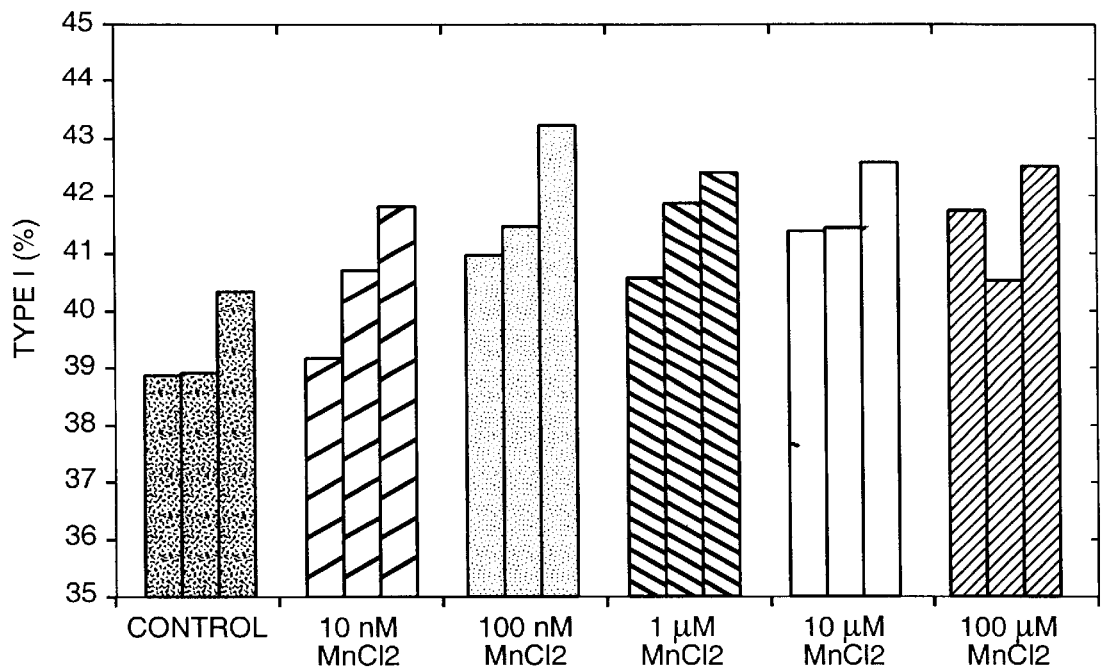
FIG._10A
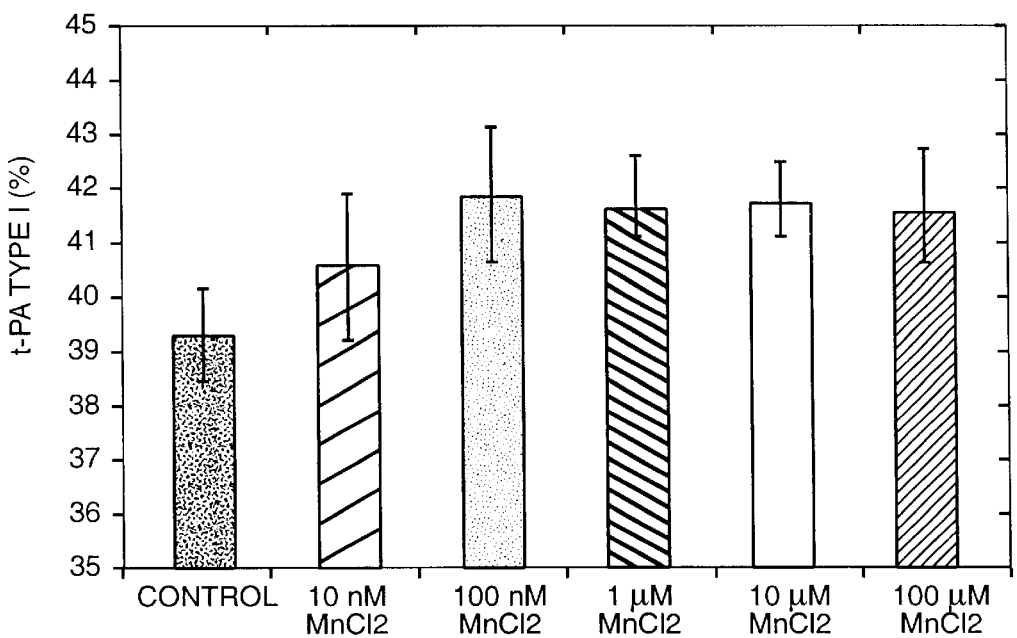
FIG._10B

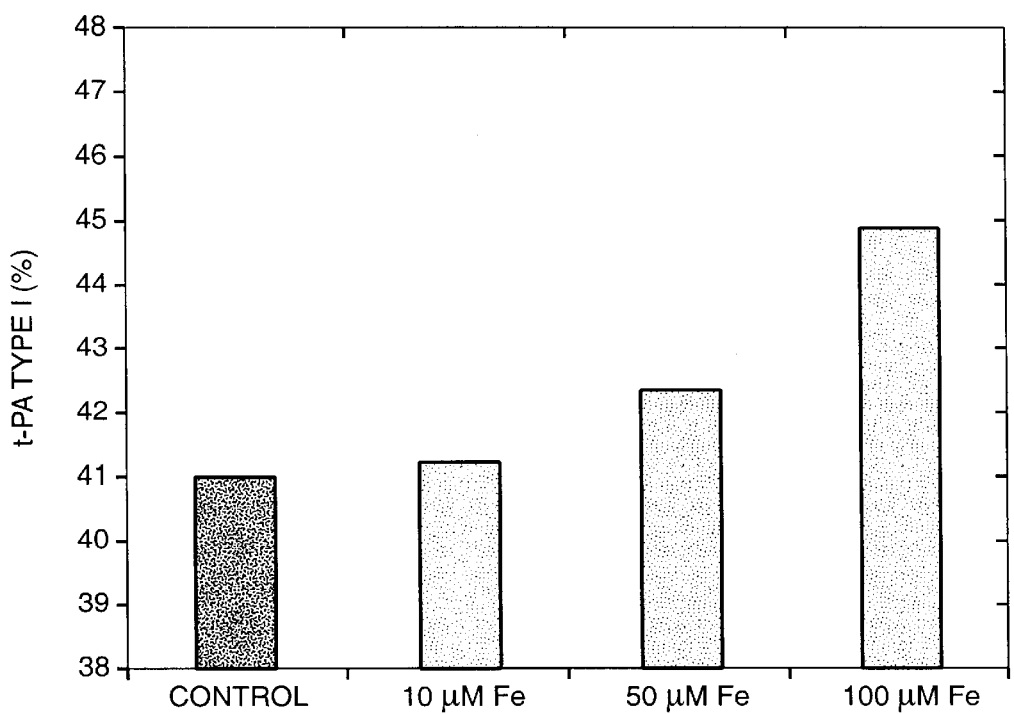
FIG._11
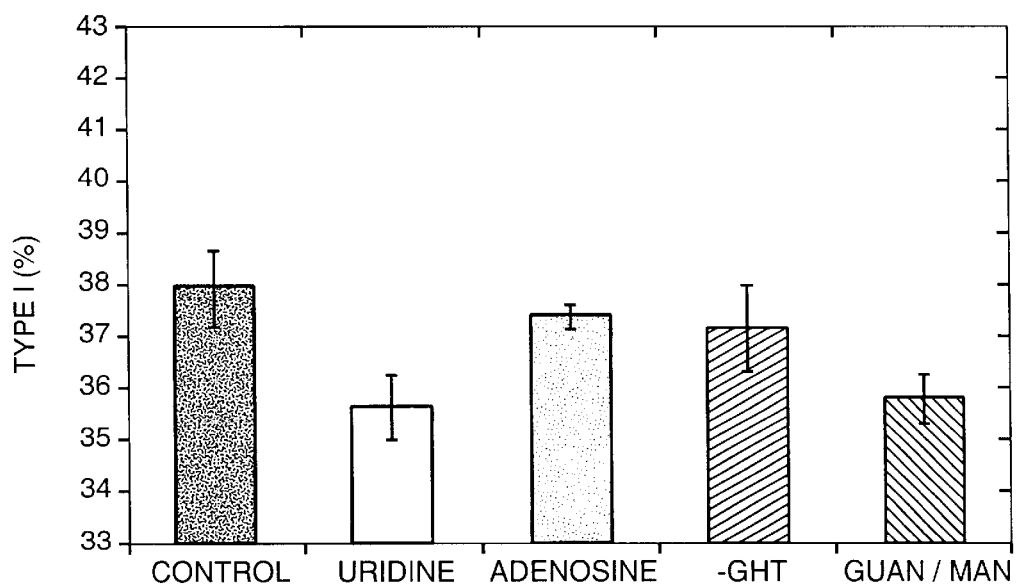
FIG._12

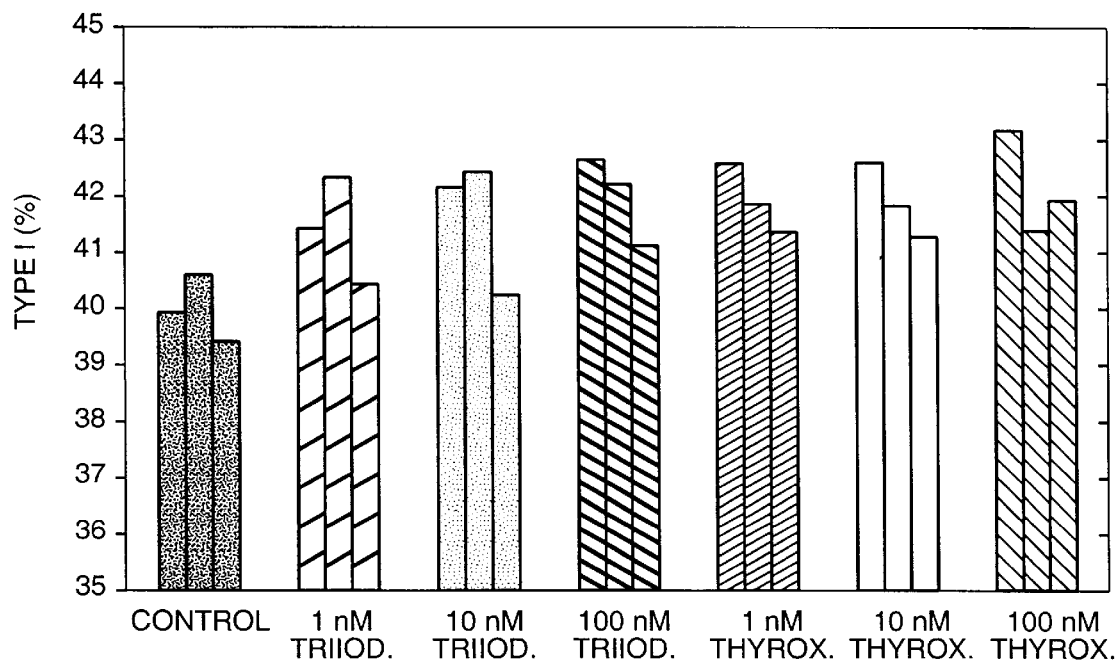
FIG._13A
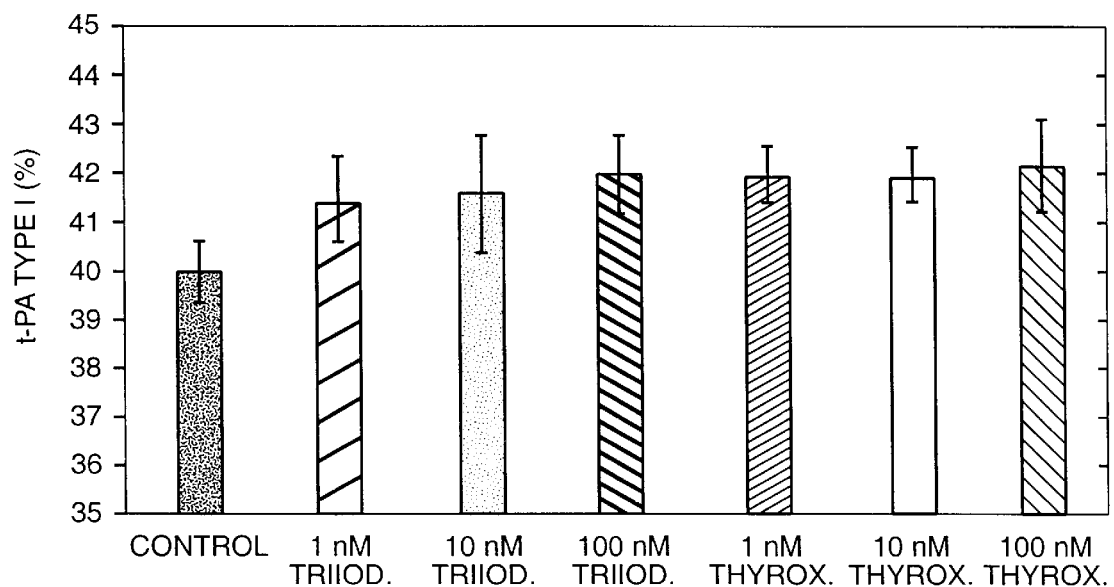
FIG._13B

CELL CULTURE PROCESS

This is a divisional application claiming priority to application Ser. No. 09/553,924, filed Apr. 21, 2000, which claims priority to U.S. Provisional Application Serial No. 60/131,076, filed Apr. 26, 1999, the entire disclosure of which is hereby incorporated by reference.

BACKGROUND OF THE INVENTION

1. Field of the Invention

The present invention concerns a process for the production of glycoproteins in mammalian cell culture. More specifically, the invention provides a process for producing glycoproteins in mammalian cells that results in enhanced occupancy of an N-linked glycosylation site occupied only in a fraction of a glycoprotein. A process for increasing the fraction of Type I tissue plasminogen activator (t-PA) in a mammalian cell culture is specifically disclosed.

2. Description of Related Disclosures and Technology

Glycoproteins

Glycoproteins, many of which have been produced by techniques of recombinant DNA technology, are of great importance as diagnostic and therapeutic agents. In a eukaryotic cell environment, glycosylation is attached to a secreted or membrane-spanning protein by co- and post-translational modification. Proteins destined for the cell surface are first co-translationally translocated into the lumen of the endoplasmic reticulum (ER) mediated by a signal sequence at or near the amino terminus of the nascent chain. Inside the ER, the signal sequence is usually removed and a high-mannose core oligosaccharide unit is attached to the asparagine (N) residue(s) present as part of the sequence Asn-X-Ser/Thr, where X is any amino acid except, perhaps, proline.

The efficiency of this co-translational glycosylation step is dependent on the presentation of an appropriate conformation of the peptide chain as it enters the endoplasmic reticulum (Imperiali and O'Connor, *Pure & Applied Chem.,* 70: 33–40 (1998)). Potential N-linked glycosylation sites may no longer be accessible after the protein has folded (Kornfeld & Kornfeld, *Ann Rev. Biochem.* 54:631–664 (1985)). Proteins next move from the ER to the Golgi apparatus where further modifications, such as sulfation and processing of the high-mannose oligosaccharide chain to a complex-type oligosaccharide, occur and the proteins are directed to their proper destinations.

N-linked oligosaccharides can have a profound impact on the pharmaceutical properties of glycoprotein therapeutics (e.g., in vivo half-life and bioactivity). Different bioprocess parameters (e.g., bioreactor type, pH, media composition, and ammonia) have been shown to affect protein glycosylation significantly. Changes in terminal glycosylation (sialylation and galactosylation) and N-glycan branching are the most frequently observed alterations.

The Carbohydrate Structure of Tissue Plasminogen Activator

Tissue plasminogen activator (t-PA), a glycoprotein, is a multidomain serine protease whose physiological role is to convert plasminogen to plasmin, and thus to initiate or accelerate the process of fibrinolysis. Initial clinical interest in t-PA was raised because of its relatively high activity in the presence, as compared to the absence, of fibrin. Wild-type t-PA is a poor enzyme in the absence of fibrin, but the presence of fibrin strikingly enhances its ability to activate plasminogen. Recombinant human t-PA is used therapeutically as a fibrinolytic agent in the treatment of acute myocardial infarction and pulmonary embolism, both conditions usually resulting from an obstruction of a blood vessel by a fibrin-containing thrombus.

In addition to its striking fibrin specificity, t-PA exhibits several further distinguishing characteristics:

(a) T-PA differs from most serine proteases in that the single-chain form of the molecule has appreciable enzymatic activity. Toward some small substrates, and toward plasminogen in the absence of fibrin, two-chain t-PA has greater activity than one-chain t-PA. In the presence of fibrin, however, the two forms of t-PA are equally active (Rijken et al., *J. Biol. Chem.,* 257: 2920–2925 (1982); Lijnen et al., *Thromb. Haemost.,* 64: 61–68 (1990); Bennett et al., *J. Biol. Chem.,* 266: 5191–5201 (1991)). Most other serine proteases exist as zymogens and require proteolytic cleavage to a two-chain form to release full enzymatic activity.

(b) The action of t-PA in vivo and in vitro can be inhibited by a serpin, PAI-1 (Vaughan et al., *J. Clin. Invest.,* 84: 586–591 (1989); Wiman et al., *J. Biol. Chem.,* 259: 3644–3647 (1984)).

(c) T-PA binds to fibrin in vitro with a $K_d$ in the $\mu$M range.

(d) T-PA has a rapid in vivo clearance that is mediated by one or more receptors in the liver (Nilsson et al., *Thromb. Res.,* 39: 511–521 (1985); Bugelski et al., *Throm. Res.,* 53: 287–303 (1989); Morton et al., *J. Biol. Chem.,* 264: 7228–7235 (1989)).

A substantially pure form of t-PA was first produced from a natural source and tested for in vivo activity by Collen et al., U.S. Pat. No. 4,752,603 issued Jun. 21, 1988 (see also Rijken et al., *J. Biol. Chem.,* 256: 7035 (1981)). Pennica et al. (*Nature,* 301: 214 (1983)) determined the DNA sequence oft-PA and deduced the amino acid sequence from this DNA sequence (U.S. Pat. No. 4,766,075 issued Aug. 23, 1988).

Human wild-type t-PA has potential N-linked glycosylation sites at amino acid positions 117, 184, 218, and 448. Recombinant human t-PA (ACTIVASE® t-PA) produced by expression in CHO cells was reported to contain approximately 7% by weight of carbohydrate, consisting of a high-mannose oligosaccharide at position 117, and complex oligosaccharides at Asn-184 and Asn-448 (Vehar et al., "Characterization Studies of Human Tissue Plasminogen Activator produced by Recombinant DNA Technology," *Cold Spring Harbor Symposia on Quantitative Biology,* LI:551–562 (1986)).

Position 218 has not been found to be glycosylated in native t-PA or recombinant wild-type t-PA. Sites 117 and 448 appear always to be glycosylated, while site 184 is thought to be glycosylated only in a fraction of the molecules. The t-PA molecules that are glycosylated at position 184 are termed Type I t-PA, and the molecules that are not glycosylated at position 184 are termed Type II t-PA. In melanoma-derived t-PA, the ratio of Type I to Type II t-PA is about 1:1. The most comprehensive analysis of the carbohydrate structures of CHO cell-derived human t-PA was carried out by Spellman et al., *J. Biol. Chem.,* 264: 14100–14111 (1989), who showed that at least 17 different Asn-linked carbohydrate structures could be detected on the protein. These ranged from the high-mannose structures at position 117 to di-, tri-, and tetra-antennary N-acetyllactosamine-type structures at positions 184 and 448. Type I and Type II t-PAs were reported to be N-glycosylated in an identical way at Asn-117 and Asn-448 positions, when isolated from the same cell line. For further details, see also Parekh et al., Biochemistry, 28: 7644–7662 (1989). The specific fibrinolytic activity of Type II t-PA has been shown to be about 50% greater than that of Type I t-PA (Einarsson et al., *Biochim. Biophys. Acta*, 830: 1–10 (1985)). Further, increased Type I is correlated with increased half-life (Cole et al., *Fibrinolysis*, 7: 15–22 (1993)). However, Type II t-PA, which lacks a portion of carbohydrate associated with Type I t-PA, as well as desialated t-PA, demonstrated a longer T½ beta than standard t-PA (Beebe and Aronson, *Thromb. Res.* 51: 11–22 (1988)).

Analysis of the sequence of t-PA has identified the molecule as having five domains. Each domain has been defined with reference to homologous structural or functional regions in other proteins such as trypsin, chymotrypsin, plasminogen, prothrombin, fibronectin, and epidermal growth factor (EGF). These domains have been designated, starting at the N-terminus of the amino acid sequence of t-PA, as the finger (F) domain from amino acid 1 to about amino acid 44, the growth factor (G) domain from about amino acid 45 to about amino acid 91 (based on homology with EGF), the kringle-1 (K1) domain from about amino acid 92 to about amino acid 173, the kringle-2 (K2) domain from about amino acid 180 to about amino acid 261, and the serine protease (P) domain from about amino acid 264 to the carboxyl terminus at amino acid 527. These domains are situated essentially adjacent to each other, and are connected by short "linker" regions. These linker regions bring the total number of amino acids of the mature polypeptide to 527, although three additional residues (Gly-Ala-Arg) are occasionally found at the amino terminus. This additional tripeptide is generally thought to be the result of incomplete precursor processing, and it is not known to impart functionality. Native t-PA can be cleaved between position 275 and position 276 (located in the serine protease domain) to generate the two-chain form of the molecule.

Each domain contributes in a different way to the overall biologically significant properties of the t-PA molecule. Domain deletion studies show that the loss of the finger, growth factor, or kringle-2 domain results in a lower-affinity binding of the variant t-PA to fibrin (van Zonneveld et al., Proc. Natl. Acad. Sci. USA, 83: 4670–4674 (1986); Verheijen et al., *EMBO J.*, 5: 3525–3530 (1986)); however, more recent results obtained with substitution mutants indicate that the kringle-2 domain is less involved in fibrin binding than earlier expected (Bennett et al., supra). The domain deletion studies have implicated the finger and growth factor domains in clearance by the liver (Collen et al., *Blood*, 71: 216–219 (1988); Kalyan et al., *J. Biol. Chem.*, 263: 3971–3978 (1988); Fu et al., *Thromb. Res.*, 50: 33–41 (1988); Refino et al., *Fibrinolysis*, 2: 30 (1988); Larsen et al., *Blood*, 73: 1842–1850 (1989); Browne et al., *J. Biol. Chem.*, 263: 1599–1602 (1988)). The kringle-2 domain is responsible for binding to lysine. The serine protease domain is responsible for the enzymatic activity of t-PA and contains specific regions where mutations were shown to affect both fibrin binding and fibrin specificity (possibly direct interactions with fibrin), and other regions where only fibrin specificity is altered (possibly indirect interactions with fibrin) (Bennett et al., supra). Studies with mutants resulting from site-directed alterations indicate the involvement of the glycosylation of t-PA in clearance (Lau et al., *Bio/Technology*, 5: 953–958 (1987); Lau et al., *Bio/Technology*, 6: 734 (1988)).

An unglycosylated variant of t-PA consisting of the kringle-2 and protease domains was described to have a slower plasma clearance than wild-type t-PA (Martin et al., *Fibrinolysis*, 4:(Suppl.3):9 (Abstract 26) (1990)). The effects of altering oligosaccharide structures at sites 164 and 448 of t-PA were also examined by Howard et al., *Glycobiology*, 1: 411–418 (1991). Hotchkiss et al. (*Thromb. Haemost.*, 60: 255–261 (1988)) selectively removed oligosaccharide residues from the t-PA molecule, and demonstrated that the removal of these residues decreased the rate of clearance of t-PA. These researchers, and Lau et al. ((1987), supra, (1988), supra) also generated the t-PA variant N117Q (wherein asparagine at position 117 of wild-type human t-PA was substituted with glutamine) to prevent glycosylation at position 117. This variant, similarly to that obtained by enzymatic removal of the high-mannose oligosaccharide at this position, exhibited an about two-fold slower clearance rate than wild-type human t-PA. See also EP-A 238,304 published Sep. 23, 1987 and EP-A 227,462 published Jul. 1, 1987.

Several reports have suggested that the carbohydrate moieties of t-PA influence the in vitro activity of this enzyme (Einarsson et al., supra; Opdenakker et al., *Proc. Sci. Exp. Biol. Med.*, 182: 248–257 (1986)). T-PA is endocytosed by mannose receptors of liver endothelial cells and by galactose receptors of parenchymal cells. Indeed, the in vivo clearance of recombinant human t-PA produced in mammalian cell cultures was influenced by carbohydrate structures, particularly by the high-mannose oligosaccharides (Hotchkiss et al., supra). A t-PA variant (designated TNK t-PA) that has a glycosylation site added at amino acid position 103, the native glycosylation site removed at amino acid position 117, and the sequence at amino acid positions 296–299 of native human t-PA replaced by AAAA, has been shown to have increased circulatory half-life, and markedly better fibrin specificity than wild-type human t-PA (Keyt et al., *Proc. Natl. Acad. Sci. USA*, 91: 3670–3674 (1994)).

Glycoproteins Other than Native t-PA with More than One Glyoform

Cells expressing tPA-6, a molecule composed of the kringle-2 and serine protease domains of t-PA, process it into two glycoforms, a monoglycosylated form with Asn-448 occupied, and a diglycosylated form with Asn-448 and Asn184 occupied (Berg et al., *Blood*, 81: 1312–1322 (1993)).

Plasminogen exists in two glycoforms. The more glycosylated form, commonly referred to as "plasminogen-1," "plasminogen I," or "Type 1 plasminogen," has a galactosamine-based oligosaccharide attached at amino acid position 345 (Thr345) and a complex glycosamine-based oligosaccharide at amino acid position 288 (Asn288) of a native human plasminogen molecule. The less glycosylated form, commonly referred to as "plasminogen-2," "plasminogen II," or "Type 2 plasminogen," has a single oligosaccharide chain attached at amino acid position 345 (Thr345) (Hayes and Castellino, *J. Biol. Chem.*, 254(18): 8772–8776, 8777–8780 (1979); Lijnen et al., *Eur. J. Biochem.*, 120: 149–154 (1981); Takada et al., *Thrombosis Research*, 39: 289–296 (1985)).

Other glycoproteins displaying variable site occupancy (variations in N- and O-glycosylation site-occupancy) include granulocyte-macrophage colony-stimulating factor (Okamoto et al., *Archives of Biochemistry and Biophysics*, 286:562–568 (1991)), interferon-gamma (Curling et al., *Biochem. J.*, 272: 333–337 (1990)), protein C (Miletich and Broze, *J. Biol. Chem.*, 265: 11397–11404 (1990)), and interleukin-2. Glycosylation of gamma-interferon was stable throughout an optimized culture design strategy using fed-batch cultures, with exposure to glucose starvation possibly leading to a dramatic change in glycosylation efficiency (Xie et al., *Biotechnol. Bioeng.*, 56: 577–582 (1997)).

Different factors have been discussed to be potentially responsible for variable site-occupancy, including availability of dolichol-phosphate and nucleotide sugars (Nyberg et al., *Biotechnol. Bioeng.,* 62: 336–347 (1999)), glycosyltransferase activity (Hendrickson and Imperiali, *Biochemistry,* 34: 9444–9450 (1995); Kaufman et al., *Biochemistry,* 33: 9813–9819 (1994)), and variable glycosylation site accessibility due to competition with protein folding (Holst et al., *The EMBO J.,* 15: 3538–3546 (1996); Imperiali, *Acc. Chem. Res.,* 30: 452–459 (1997); Shelikoff et al., *Biotechnol. Bioeng.,* 50: 73–90 (1996)). Any of these factors could be influenced by cell culture conditions. T-PA site-occupancy usually varies within a rather narrow range (±5%).

Studies of Oligosaccharyltransferase/Metal-gations in Glycosylation

Asparagine-linked glycosylation involves the enzyme-catalyzed modification of an asparagine side chain in a nascent polypeptide with a tri-antennary tetradecasaccharide moiety. This first committed step in the biosynthesis of N-linked glycoproteins is catalyzed by oligosaccharyltransferase, a heteromeric membrane-associated enzyme complex found in the lumen of the endoplasmic reticulum of eukaryotic cells. See Imperiali, supra; Allen et al., *J. Biol. Chem.,* 270: 4797–4804 (1995); Sharma et al., *Eur. J. Biochem.,* 116: 101–108 (1981); Silberstein and Gilmore, *The FASEB Journal,* 10: 849–858 (1996); Kumar el al., *Biochem. Mol. Biol. Intl.,* 36: 817–826 (1995); Bause et al., *Biochem. J.,* 312: 979–985 (1995); Xu and Coward, *Biochemistry,* 36: 14683–14689 (1997); Kumar et al., *Biochem. Biophys. Res. Comm.,* 247: 524–529 (1998); Watt et al., *Curr. Op. Struct. Biol.,* 7: 652–660 (1997).

For optimal activity, oligosaccharyltransferase requires a small amount of manganese divalent ion, but other divalent metal cations with an octahedral coordination geometry will support transfer, although at reduced rates (Hendrickson and Imperiali, supra; Kaufman et al., supra; Kumar et al., *Biochem. & Mol. Biol. International,* 36: 817–826 (1995)).

The Role of Temperature in Mammalian Cell Cultures

To simulate normal body environment, fermentor temperature in cultivating mammalian cells is controlled almost exclusively at 37° C. This dogma is so widely accepted that, so far, little attention has been paid to varying temperature in the cell culture process. The scarce literature data suggest that reduced fermentor temperature results in improved cell viability and shear resistance, higher cell density and titer in batch cultures, and a reduction in glucose/lactate metabolism (Chuppa et al., *Biotechnol. Bioeng.,* 55: 328–338 (1997)).

Specifically, Reuveny et al., *J. Immunol. Methods,* 86: 53–59 (1986) studied the effect of temperatures in the range of 28° C. to 37° C. on batch hybridoma cell cultures. They found that although at lower temperatures the cell viability was improved, this was accompanied by a decrease in glucose uptake and a decrease in the specific antibody production. Therefore, in this particular case, lower temperatures did not enhance the overall performance of the cell culture process.

Sureshkumar and Mutharasan, *Biotechnol. Bioeng.,* 37: 292–295 (1991) investigated the effect of the temperature range of 29° C. to 42° C. on the cell culture process, and found that maximum cell density was achieved at 33° C. In contrast, the glucose uptake and specific lactate production rates were dramatically lower at 33° C. than at 39° C. These results showed that the optimal temperatures for growth and productivity may considerably differ. While the viability increase at temperatures below 37° C. appears to be a general phenomenon, the effect of temperature on specific productivity has been shown to be cell-line dependent (Chuppa et al., supra).

Weidemann et al., *Cytotechnology,* 15: 111–116 (1994) cultivated adherent recombinant baby hamster kidney (BHK) cells at temperatures between 30° and 37° C. The low-temperature cultivation in batch and repeated batch mode in a two-liter bioreactor showed a lower growth rate and a lower glucose consumption rate (i.e., less lactate production). On the other hand, the maximum cell density and productivity were not affected by the temperature reduction.

Kretzmer et al., "Cultivation Temperature-Effect on Cell Culture Processes and Their Optimization" (American Chemical Society Meeting, San Francisco, Calif.), abstract 138, presented Apr. 16, 1997, disclosed the effect of cultivation temperature on cell culture processes and their optimization, but apparently no specific glycosylation analysis.

It has been suggested that reduced fermentor temperatures might have other advantages related to product quality and integrity, but the effect of low temperatures on product quality, and in particular, on protein glycosylation, has been scarcely studied. Chuppa et al., supra, have reported that fermentation temperature did not have a significant effect on the sialic acid content of glycoproteins. Although the total sugar content was somewhat lower at 37° C. than at 34° C. or 35.5° C., the authors viewed this difference as "not substantial."

However, U.S. Pat. No. 5,705,364 described preparing glycoproteins by mammnalian cell culture wherein the sialic acid content of the glycoprotein produced was controlled over a broad range of values by manipulating the cell culture environment, including the temperature. The host cell was cultured in a production phase of the culture by adding an alkanoic acid or salt thereof to the culture at a certain concentration range, maintaining the osmolality of the culture at about 250 to about 600 mOsm, and maintaining the temperature of the culture between about 30 and 35° C.

Bahr-Davidson, "Factors Affecting Glycosylation Site Occupancy of ASN- 184 of Tissue-Type Plasminogen Activator Produced in Chinese Hamster Ovary Cells," A Dissertation submitted to the Department of Chemical Engineering and the Committee of Graduate Studies of Stanford University in Partial Fulfillment of the Requirements for the Degree of Doctor of Philosophy, May 1995, investigated the effects of temperature on glycosylation site occupancy and reported that site occupancy was increased by exposing cells to 26° C. (see pages 50–51).

Hormonal and Other Treatments to Influence Glycosylation

The effect of various additives such as components of plasma to the culture media on protein production and glycosylation has been studied in the literature, for example, the effects of hormonal treatments on membrane glycosylation in rat kidney brush broder membranes (Mittal et al., *Indian J. Exper. Biol.,* 34: 782–785 (1996)). Studies of Muc-1 mucin expression established the hormonal basis for MRNA expression (Parry et al., *J. Cell Sci.,* 101: 191–199 (1992)). Thyroid hormone regulation of alpha-lactalbumin with differential glycosylation has been reported (Ziska et al., *Endocrinology,* 123: 2242–2248 (1988)). The cellular response to protein N-glycosylation was increased in the presence of thyroxine, insulin, and thrombin, and the effect was dose-dependent (Oliveira and Banerjee, *J. Cell. Physiol.,* 144: 467–472 (1990)). Thyroxine was found to induce changes in the glycosylation pattern of rat alpha-fetoprotein (Naval et al., *Int. J. Biochem.,* 18: 115–122 (1986)).

In addition to hormonal treatments, glutatb one and glucose-6-phosphate dehydrogenase deficiency increased protein glycosylation (Jain, *Free Radical Biology & Medicine*, 24: 197–201 (1998)). Thyrotropin was found to control oligosaccharyltransferase activity in thyroid cells (Desruisseau et al., *Mol. Cell. Endocrinol.*, 122: 223–228 (1996)). The addition of glucose and tri-iodothyronine ($T_3$) to a medium producing a pro-urokinase derivative improved productivity (Hosoi et al., *Cytotechnoloy*, 19: 1–10 (1996)). Also, fucosyltransferase activity in the rat small intestine was responsive to hydrocortisone regulation during the suckling period (Biol et al., *Biochim. Riophys. Acta*, 1133: 206–212 (1992)). Hydrocortisone treatment also induced quantitative alterations in glycosylation of mouse mammary tumor virus precursors (Maldarelli and Yagi, *JNCI*, 77: 1109–1115 (1986)). Glycosylation of cellular glycoconjugates in a carcinoma cell line was enhanced by a retinoic acid (Sacks et al., *Glycoconjugate J.*, 13: 791–796 (1996)). Further, retinoic acid had reversible effects on glycosaminoglycan synthesis during differentiation of HL-60 leukemia cells (Reiss et al., *Can Res.*, 45: 2092–2097 (1985)). Additionally, retinoic acid, as well as hydrocortisone, was found to modulate glycosaminoglycan synthesis of human malignant keratinocytes (Reiss et al., *J. Invest. Dermatol.*, 86: 683–688 (1986)).

The competition between folding and glycosylation in the endoplasmic reticulum has been described (Holst et al., supra), as has acute heat shock inducing the phenomenon of prompt glycosylation (Jethmalani et al., *J. Biol. Chem.*, 269: 23603–23609 (1994)).

There is a need for increasing glycosylation site occupancy in glycoproteins having multiple glycoforms to produce glycoprotein therapeutics of consistent product quality. For example, there is a need to increase the fraction of Type I t-PA in the t-PA production process. Such increase in site-occupancy generates t-PA with activity more closely resembling the international human t-PA standard, and thus more closely resembling human t-PA. Type I t-PA is also more soluble than Type II, which may be of some value in processing steps. Further, increased Type I is correlated with increasing circulatory half-life, as noted above.

SUMMARY OF THE INVENTION

It has been found that during the production of a wild-type glycoprotein, namely human t-PA, in mammalian cells, namely Chinese Hamster Ovary (CHO) cells, use of certain divalent metals, hormones, or factors that manipulate cell-cycle distribution to control or influence glycosylation significantly increases site occupancy of a glycosylation site of the glycoprotein. For example, decreasing the cultivation temperature from 37° C. to about 30–35° C. in the production phase significantly enhances the occupancy of the glycosylation site at amino acid position 184, and thereby increases the ratio of Type I t-PA to Type II t-PA. Specifically, decreasing the temperature from 37 to 33 or 31° C. increased t-PA site-occupancy up to 6%. Temperatures below 37° C. are expected similarly to facilitate the occupancy of not-easily-accessible N-linked glycosylation sites in other glycoproteins. Accordingly, temperature can be used as a sensitive tool for fine tuning the ratio of variously glycosylated forms of glycoproteins having one or more N-linked glycosylation sites occupied only in a fraction of the protein.

In addition, other environmental factors, including those that manipulate the culture's growth state, and correspondingly cell-cycle distribution, such as butyrate, or a cell-cycle inhibitor that increases the proportion of cells in the G0/G1 phase such as quinidine, plasma components such as thyroid hormones, and/or certain divalent metal cations significantly elevated the t-PA Type I content (about 1–2.5%) compared to control conditions, and are expected to act similarly with respect to other glycoproteins. In contrast, addition of the relevant nucleoside precursor molecules (e.g., uridine, guanosine, mannose) did not result in improved site-occupancy.

In one aspect, the invention concerns a process for producing a glycoprotein comprising culturing mammalian host cells producing the glycoproteins (i.e., cells expressing nucleic acid encoding the glycoprotein) in the presence of (a) a factor that modifies growth state in a cell culture, (b) a divalent metal cation that can adopt and prefers an octahedral coordination geometry, or (c) a plasma component, whereby the occupancy of an N-linked glycosylation site occupied only in a fraction of the glycoprotein is enhanced in the glycoprotein so produced. Preferably, the factor is a cell-cycle inhibitor that blocks cells in the G0/G1 phase, a butyrate salt, and/or a temperature of the culture of between about 30 and 35° C., the divalent cation is manganese or iron, and the plasma component is a hormone. Preferably, the cell culture procedure includes a growth phase, followed by a transition phase and a production phase. In a preferred embodiment, in the growth phase the mammalian host cells are cultured at about 37° C., whereupon, during the transition phase, the temperature is lowered to between about 30° C. and 35° C. The host cells preferably are CHO cells, and the glycoprotein preferably is t-PA.

In another aspect, the invention provides a process for producing human t-PA comprising culturing CHO cells expressing nucleic acid encoding said t-PA in a serum-free medium in a production phase at a temperature of between about 30° C. and 35° C. and in the presence of about 0 to 2 mM of a butyrate salt, whereby the occupancy of an N-linked glycosylation site occupied only in a fraction of t-PA is enhanced in the t-PA so produced:

In a still further aspect, the invention supplies a process for producing human t-PA comprising culturing CHO cells expressing nucleic acid encoding said t-PA in a serum-free medium in a growth phase at a temperature of about 37–40° C., wherein said medium comprises from about 10 nM to 100 μM of adivalent metal cation that can adopt and prefers an octahedral coordination geometry; culturing said cell in a transition phase at a temperature of about 37–40° C.; and culturing said cell in a production phase wherein after about 48 hours into the production phase the temperature is lowered to between about 30° C. and 35° C. and about 0.75 to 1.5 mM of a butyrate salt is added to the medium, whereby the occupancy of an N-linked glycosylation site occupied only in a fraction of t-PA is enhanced in the t-PA so produced. In this process, a plasma component such as a thyroid hormone, e.g., thyroxine or tri-iodothyronine, or a cell-cycle inhibitor that blocks cells in the G0/G1 phase such as quinidine is optionally added to the culture medium before or during the growth phase.

Hence, the process herein facilitates the production of a preferred glycoform of a glycoprotein, such as Type I t-PA, in a mammalian cell culture, and also increases the ratio of preferred to non-preferred glycoproteins, such as the ratio of Type I to Type II t-PA, in a mammalian cell culture.

BRIEF DESCRIPTION OF THE DRAWINGS

FIG. 1 shows a depiction of Type I t-PA and Type II t-PA and a chromatogram thereof.

FIG. 2 shows the percentage of Type I human t-PA in cell cultures of CHO cells cultivated at various scales at 37° C.

FIG. 3 shows graphs of the percentage of Type I human t-PA in cell cultures of CHO cells at 37° C. as a function of 12K-fermentation run time, with each graph line representing a different run.

FIGS. 4A and 4B show the percentage of Type I human t-PA in cell cultures of CHO cells cultivated on a laboratory scale (in 25 cm$^2$ T-flasks and 100-ml spinner flasks-FIG. 4A) or in a 5-liter bioreactor (FIG. 4B for 5–7 days at 33° C. relative to control (cell culture kept at 37° C.).

FIG. 5 shows the percentage of Type I human t-PA in cell cultures of CHO cells cultivated in T-flasks at 37° C. for 34 days wherein sodium butyrate is added in the amount indicated at the time of inoculation. The values are from triplicate experiments.

FIG. 6 shows the percentage of Type I human t-PA in cell cultures of CHO cells cultivated in 60-mm culture dishes at 37° C. for 4–6 days wherein temperature changes with or without sodium butyrate are compared (wherein 37° C.1— means control at 37° C. with no butyrate; 37° C.11× is at 37° C. with 0.75 mM butyrate, 37° C.12× is at 37 ° C. with 1.5 mM butyrate, 33° C.1—is at 33° C. with no butyrate, 33° C.11× is at 33° C. with 0.75 mM butyrate, 33° C.12× is at 33° C. with 1.5 mM butyrate, 31° C.1—is at 31° C. with no butyrate, 31° C.11× is at 31° C. with 0.75 mM butyrate, and 31° C.12× is at 31° C. with 1.5 mM butyrate).

FIG. 7 shows percentage of Type I human t-PA in cell cultures of CHO cells cultivated in 5-liter bioreactors after 5–7 days, wherein temperature changes with or without sodium butyrate are compared (where control is at 37° C. without butyrate, 33° C. is at 33° C. without butyrate, 2× butr. is at 37° C. with 1.5 mM butyrate, and 33° C./2× is at 33° C. with 1.5 mM butyrate).

FIG. 8 shows the percentage of Type I human t-PA in cell cultures of CHO cells cultivated in fermentors over time at 37° C. in which sodium butyrate was added to a concentration of 0.75 mM at approximately 48 hours, and the percentages of cells in G0/G1 phase at the corresponding time points. These results reflect the averages of three separate cultures.

FIG. 9 shows the percentage of Type I human t-PA in cell cultures of CHO cells cultivated in T-flasks at 37° C. for 3–4 days wherein at the time of inoculation no cell-cycle inhibitor is added (control), thymidine (250 μg/mL) is added, or quinidine (90 μM) is added. The values are from triplicate experiments.

FIGS. 10A and 10B show the percentage of Type I human t-PA in cell cultures of CHO cells cultivated in 60-mm culture dishes at 37° C. for 4–6 days wherein at the time of inoculation 3 nM of MnCl$_2$ is added (control), or 10 nM, 100 nM, 1 μM, 10 μM, or 100 μM MnCl$_2$ is added. The values are expressed in triplicate for FIG. 10A and as an average of triplicates for FIG. 10B.

FIG. 11 shows the percentage of Type I human t-PA in cell cultures of CHO cells cultivated in 60-mm culture dishes at 37° C. for 4–6 days wherein at the time of inoculation no ferric citrate is added (control), or 10 μM ferric citrate, 50 μM ferric citrate, or 100 μM ferric citrate is added.

FIG. 12 shows the percentage of Type I human t-PA in cell cultures of CHO cells cultivated in 60-mm culture dishes at 37° C. for 4–6 days wherein the cells are cultivated in the presence of increased amounts of specified nucleotide sugar precursor molecules.

FIGS. 13A and 13B show the percentage of Type I human t-PA in cell cultures of CHO cells cultivated in 60-mm culture dishes at 37° C. for 7 days wherein at the time of inoculation no hormone is added (control), or 1 nM, 10 nM, or 100 nM of tri-iodothyronine (Triiod.) or of thyroxine (Thyrox.) is added. The values are expressed in triplicate for FIG. 13A and as an average of triplicates for FIG. 13B.

DETAILED DESCRIPTION OF THE INVENTION

I. Definitions

As used herein, the word "enhanced" as it relates to occupancy of an N-linked glycosylation site occupied only in a fraction of the glycoprotein refers to relative value obtained by practicing the current invention versus control value obtained by not using the parameters of this invention. The value is calculated based on the percentage of glycosylation sites occupied at the particular position of the glycoprotein in question versus a baseline value, which is determined without using the factors, cations, or plasma components herein claimed. For example, t-PA is secreted as a mixture of two major glycoforms, Type I (all three N-glycosylation sites are occupied) and Type II (Asn-184 is not occupied), and an enhanced occupancy level means an increased site occupancy such that the mixture has increased amounts of Type I relative to Type II t-PA versus the control. This occupancy level can be measured, for example, by using reversed-phase high-pressure liquid chromatography (RP-HPLC) to elute the fragments of the different types of glycoprotein (the types having different glycosylation site occupancy levels) and integrating the peak areas for each type of glycoprotein to determine relative quantities. The most typical way to express these quantities is by the percentage of the higher-occupancy type of glycoprotein to total types of glycoprotein. A specific example of an assay used to measure enhancement for Type I/Type II t-PA is set forth below in Example 1.

As used herein, "glycoprotein" refers generally to peptides and proteins having more than about ten amino acids and at least one glycosylation site that is occupied only in a fraction of the glycoprotein product, i.e., they display variable site-occupancy or variations in N- and O-glycosylation site-occupancy. The glycoproteins may be homologous to the host cell, or preferably, they are heterologous, i.e., foreign, to the host cell being utilized, such as a human protein produced by a CHO cell. Preferably, mammalian glycoproteins (glycoproteins that were originally derived from a mammalian organism) are used, more preferably, those which are directly secreted into the medium, and most preferably, those wherein N-glycosylation site-occupancy is involved.

The specifically-preferred glycoproteins herein are t-PA, plasminogen, interferon-gamma, Protein C, IL-2, and CSF, for example, GM-CSF. The more preferred glycoproteins are t-PA or plasminogen, and the most preferred is t-PA, more notably human t-PA.

The terms "tissue plasminogen activator", and "t-PA" refer to human extrinsic (tissue-type) plasminogen activator having fibrinolytic activity that typically has a structure with five domains (finger, growth factor, kringle-1, kringle-2, and protease domains), but nonetheless may have fewer domains or may have some of its domains repeated if it still functions as a thrombolytic agent and retains the N-linked glycosylation sites at positions 117, 184, and 448. At minimum, the t-PA consists of a protease domain that is capable of converting plasminogen to plasmin, and an N-terminal region believed to be at least partially responsible for fibrin binding, and retains the N-linked glycosylation sites at positions corresponding to amino acid positions 117, 184, and 448 of wild-type human t-PA. The retention of these glycosylation sites is due to the fact that variable site occupancy of recombinant and melanoma-derived wild-type t-PA leads to production of two variants, designated as "Type I t-PA" and "Type II t-PA", respectively. Type I t-PA contains N-linked oligosaccharides at positions 117, 184, and 448. Type II t-PA contained N-linked oligosaccharides at positions 117 and 448. See FIG. 1. It will be understood that natural allelic variations exist and can occur among individuals, as demonstrated by one or more amino acid differences in the amino acid sequence of t-PA of each individual.

The terms "wild-type human tissue plasminogen activator", "wild-type human t-PA", "native human tissue plasminogen activator," and "native human t-PA", where "human t-PA" may be abbreviated as "ht-PA", refer to native-sequence human t-PA, i.e., that encoded by the cDNA sequence reported in U.S. Pat. No. 4,766,075, issued Aug. 23, 1988. Amino acid site numbers or positions in the t-PA molecule are labeled in accordance with U.S. Pat. No. 4,766,075. The t-PA may be from any native source. In addition, the t-PA may be obtained from any recombinant expression system, including, for example, CHO cells or human embryonic kidney 293 cells.

As used herein, references to various domains of t-PA mean the domains of wild-type human t-PA as hereinabove defined, and functionally equivalent portions of human t-PA having amino acid alterations as compared to the native human t-PA sequence, or of (native or variant) t-PA from other sources, such as bat tissue plasminogen activator (bat-PA). Thus, as used herein, the term "protease domain" refers to the region extending from amino acid position 264 to amino acid position 527, inclusive, of the mature form of wild-type human t-PA, and to functionally equivalent portions of human t-PA having amino acid alterations as compared to the native human t-PA sequence, or of t-PA from other sources, such as bat-PA.

As used herein, "factor that modifies growth state in a cell culture" refers to a factor that increases the proportion of cells in the G0/G1 phase of growth such as a cell-cycle inhibitor that causes cells to accumulate or blocks the cells in the G0/G1 phase. Such factors manipulate cell cycle distribution to control or influence glycosylation. Such a factor may affect glycosylation in mechanisms beyond growth state, but are defined herein as affecting at least the growth state.

As used herein, a "cell-cycle inhibitor that blocks cells in the G0/G1 phase of growth" is a molecule that causes cells to accumulate in the G0/G1 phase of growth. This can be determined by cell cycle analysis, i.e., uniform suspensions of nuclei are stained with propidium iodide (PI) using the detergent-trypsin method of Vindelov et al., *Cytometry*, 3: 323–327 (1983) to determine relative cellular DNA content by flow cytometric analysis. Events are gated using doublet discrimination to exclude doublets, and the data are modeled using ModFit LT Cell Cycle Analysis™ software (Verity Software House). A preferred such inhibitor herein is quinidine.

By "butyrate" or "butyrate salt" is meant any corresponding salt of butyric acid, such as sodium butyrate or potassium butyrate.

By "phase" is meant a certain phase of culturing of the cells as is well recognized by the practitioner. For example, "growth phase" of the cell culture refers to the period of exponential cell growth (the log phase) where cells are generally rapidly dividing. During this phase, cells are cultured for a period of time, usually between 1–4 days, and under such conditions that cell growth is maximized. The growth cycle for the host cell can be determined for the particular host cell envisioned without undue experimentation. During the growth phase, cells are cultured in nutrient medium containing the necessary additives generally at about 30–40° C., preferably about 37° C., in a humidified, controlled atmosphere, such that optimal growth is achieved for the particular cell line. Cells are maintained in the growth phase for a period of between about one and four days, usually between about two and three days.

"Transition phase" of the cell culture refers to the period of time during which culture conditions for the production phase are engaged. During the transition phase environmental factors such as temperature are shifted from growth conditions to production conditions.

"Production phase" of the cell culture refers to the period of time during which cell growth has plateaued. During the production phase, logarithmic cell growth has ended and glycoprotein production is primary. During this period of time the medium is generally supplemented to support continued glycoprotein production and to achieve the desired glycoprotein product.

By "divalent metal cation that can adopt and prefers an octahedral coordination geometry" is meant a metal cation with two valencies that is capable of, and actually shows preference for, adopting an octahedral coordination geometry. Such cations are also characterized in that oligosaccharyltransferase can function (i.e., is activated) in their presence. Examples of such metal ions include manganese ($Mn^{2+}$), iron ($Fe^{2+}$), calcium ($Ca^{2+}$), and magnesium ($Mg^{2+}$). Divalent cations that show preferences for other coordination geometries, including nickel ($Ni^{2+}$), copper ($Cu^{2+}$), cadmium ($Cd^{2+}$), and zinc ($Zn^{2+}$), fail to activate the enzyme and at high concentrations also competitively inhibit activity in the presence of manganese. Hence, these latter cations are excluded from the definition.

By "plasma component" is meant a constituent of normal plasma. This would include growth promoters and tumor-promoting agents for endothelial cell growth, regulators of differentiation of epithelial tissues, glucagon, heparin, phorbol myristate acetate, PRL, thyroglobulin, 8Br-cAMP, thrombin, vitamin A and its derivatives (retinoids such as retinoic acid, e.g., beta-all-trans retinoic acid), glutathione, steroids such as corticosterone, cortisol, and corticoids, e.g., glucocorticoids such as hydrocortisone, and hormones, preferably those that are vital hormones of metabolism such as estrogen, insulin, and thyroid hormones, e.g., thyroxine and tri-iodothyronine ($T_3$). The thyroid hormones are preferred, and most preferably thyroxine and tri-iodothyronine. Since some serum, including fetal calf serum, contains thyroid hormones and the thyroid hormone binding protein at nanomolar levels, it is preferred to use serum-free medium, particularly if thyroid hormones are employed to enhance site-occupancy.

The terms "cell culture medium," "culture medium," and "fermentation medium" refer to a nutrient solution used for growing mammalian cells that typically provides at least one component from one or more of the following categories:

1) an energy source, usually in the form of a carbohydrate such as glucose;

2) all essential amino acids, and usually the basic set of twenty amino acids plus cysteine;

3) vitamins and/or other organic compounds required at low concentrations;

4) free fatty acids; and 5) trace elements, where trace elements are defined as inorganic compounds or naturally-occurring elements that are typically required at very low concentrations, usually in the micromolar range.

The cell culture medium is generally "serum free" when the medium is essentially free of serum from any mammalian source (e.g. fetal bovine serum (FBS)). By "essentially free" is meant that the cell culture medium comprises between about 0–5% serum, preferably between about 0–1% serum, and most preferably between about 0–0.1% serum. Advantageously, serum-free "defined" medium can be used, wherein the identity and concentration of each of the components in the medium is known (i.e., an undefined component such as bovine pituitary extract (BPE) is not present in the culture medium).

In the context of the present invention the expressions "cell", "cell line", and "cell culture" are used interchangeably, and all such designations include progeny. Thus, the words "transformants" and "transformed (host) cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "mammalian host cell", "host cell", "mammalian cell", "mammalian recombinant host cell," and the like, refer to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described, for example, in *Mammalian Cell Culture,* Mather, J. P. ed. (Plenum Press: N.Y., 1984), and Barnes and Sato, *Cell,* 22: 649 (1980). Typically, the cells are capable of expressing and secreting large quantities of a particular glycoprotein of interest into the culture medium. Examples of suitable mammalian host cells within the context of the present invention may include CHO cells (EP 117,159, published Aug. 29, 1989; U.S. Pat. Nos. 4,766,075; 4,853,330; 5,185, 259; Lubiniecki et al., in *Advances in Animal Cell Biology and Technology for Bioprocesses,* Spier et al., eds. (1989), pp.442–451), for example, CHO derivatives such as CHO/-DHFR (Urlaub and Chasin, *Proc. Nati. Acad. Sci. USA,* 77: 4216 (1980)), CHO-K1 DUX B11 (Simonsen and Levinson, *Proc. Natl. Acad. Sci. USA* 80: 2495–2499(1983); Urlaub and Chasin, supra), and dp 12.CHO cells (EP 307,247 published Mar. 15, 1989); rat myeloma YB2/3.oAg20(WO 86/00127 published Apr. 1, 1985); mouse C127 fibroblasts (Reddy et al., DNA, 6: 461–472 (1987)); mouse sertoli cells (TM4, Mather, *Biol. Reprod.,* 23: 243–251 (1980)); human cervical carcinoma cells (HELA, ATCC CCL 2); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44–68 (1982)); MRC 5 cells; FS4 cells; and human melanoma cells (Browne et al., *Thromb. Haemost.,* 54: 422–424 (1985)). Preferred host cells include CHO-K1 DUX B11 and dp 12.CHO cells.

The CHO cells developed for large-scale production of t-PA are maintained cryogenically in a MCB/working cell bank (WCB) system as described by Wiebe et al., in *Large Scale Mammalian Cell Culture Technology,* Lubiniecki, ed., (Marcel Dekker: New York, 1990), pp. 147–160. DHFR+ CHO-K1 cells transfected with DNA encoding human t-PA have been deposited at the American Type Culture Collection, Manassas, Va. (ATCC), and are available under accession number CCL 61. A sample of another t-PA-producing CHO cell line (CHO cell line 1–15$_{15}$) has been deposited under ATCC accession number CRL 9606. The latter cell line was reported to result in human t-PA levels approaching 50 pg/cell/day.

II. Modes for Carrying Out the Invention

General and Specific Features of Invention

It has been discovered that utilizing a factor that modifies growth state in a cell culture (such as a cell-cycle inhibitor, a butyrate salt, or lowering the temperature during the production of a glycoprotein in a mammalian cell culture from 37° C. to about 30–35° C.), or utilizing a divalent metal cation that can adopt and prefers an octahedral coordination geometry, or utilizing a plasma component, enhances the occupancy of the glycosylation site at a selected and desired amino acid position of the wild-type glycoprotein.

For example, this lowering of temperature enhances the occupancy of the glycosylation site at amino acid position 184 of wild-type human t-PA and, accordingly, increases the ratio of Type I t-PA to Type II t-PA. The ability to adjust, and increase, the Type I to Type II t-PA ratio is significant, since it enables the manufacturer to produce a recombinant protein in which this ratio closely approximates the ratio present in native t-PA (about 1:1). In addition, the ratio of Type I to Type II t-PA affects the solubility and clearance rate of t-PA, and there is evidence that an increased Type I t-PA concentration somewhat increases the circulatory half-life of t-PA. It is known that the high-mannose oligosaccharide at amino acid position 117 is primarily responsible for the rapid clearance of native human t-PA. When this oligosaccharide is removed, it has been observed that Type I t-PA has a longer half-life than Type II t-PA, indicating that there is a secondary mechanism on which the extra oligosaccharide present on Type I t-PA has a positive effect. The experimental findings herein can be extended to other glycoproteins that (like t-PA) have at least one glycosylation site that is occupied only in a fraction of the glycoprotein product.

If the factor is a butyrate salt, generally the butyrate is present in a concentration of up to about 2 mM, more preferably about 0.35 to 2 mM, still more preferably about 0.75 to 1.5 mM. The concentration thereof to be selected within this range depends mainly on the temperature to which the culture is subjected and the type of glycoprotein. Hence, if for t-PA the temperature remains at about 37 ° C. or is lowered to about 33–35° C., the butyrate concentration is preferably lower than about 1.5 mM, and more preferably is about 0.3 to 1 mM, most preferably 0.75 mM. However, if for t-PA the temperature is lowered to about 30–31° C., preferably the butyrate concentration is about 1–2 mM, more preferably about 1.5 mM. This illustration shows that more than one of these factors may be operating or present in the cell culture.

In a preferred aspect, the temperature lowering and/or butyrate addition take(s) place during the production phase of the growth cycle. In such a scenario, the temperature is lowered to between about 30 and 35° C. and/or a butyrate salt is added about 48 hours into the production phase. The production phase is suitably preceded by a growth phase and a transition phase of growth cycle. During the growth phase the temperature is preferably kept at about 37° C., and/or during the transition phase the temperature of the culture is preferably lowered to between about 30° C. and 35° C., more preferably about 31–33° C., and most preferably about 31° C.

Alternatively, or additionally to the factor(s) above, the cells are cultured in the presence of a divalent cation as defined above. The choice of divalent cation to use, as well as the specific concentration thereof, depends, inter alia, on the type of glycoprotein being produced and the metal cations and other components already present in the culture medium and their respective concentrations. For example, if the glycoprotein has a number of thio groups, it is preferred to use a thiophilic metal such as manganese and iron, with iron being the most thiophilic metal. In contrast, if the glycoprotein contains more oxygen groups, then the oxophilic cations, magnesium and calcium, are preferred. If calcium ion is already present in sufficient quantities in the medium, it is not typically used for the purposes herein and a different metal cation is used. Further, the size of the metal cation may have an influence, with iron and magnesium being smaller and calcium and manganese being larger. Steric effects due to sulfur groups on the glycoprotein may dictate a cation of smaller ionic radius. The preferred divalent metal cation herein is manganese, magnesium, or iron, more preferably manganese or iron, and most preferably manganese.

The divalent metal cation is preferably present in the culture medium during the whole cultivation time, and at least is added during the growth phase. The concentration thereof generally ranges between about 10 nm and 150 $\mu$M, preferably from about 10 nm to 100 $\mu$M for manganese and from about 20 $\mu$M to 100 $\mu$M for iron.

In another alternative, alone or together with the divalent cation and/or factor, a plasma component is present during the culturing. The plasma component is typically present in an amount from about 1 nM to 15–20 $\mu$M, depending mainly on the type of glycoprotein being produced, the type of plasma component utilized, and the scale of fermentation. For example, if the plasma component is a thyroid hormone, it is preferably present in an amount of about 1–150 nM, preferably about 10–100 nM. If the plasma component is glutathione, it is preferably present at about 1–10 $\mu$M, and if hydrocortisone, it is preferably present at about 5–15 nM, preferably about 10 nM. Preferably, the plasma component is a hormone, more preferably a thyroid hormone, and most preferably thyroxine or tri-iodothyronine.

The degree of site-occupancy to be achieved for the glycoprotein is balanced against the desired degree of secretion of the glycoprotein, which is generally taken into account in selecting which factors and other components to employ, and at what concentrations or temperatures. For example, site-occupancy is generally controlled in a select range of about ±5% without affecting t-PA secretion.

Cell Culture Procedures

According to the present invention mammalian cells are cultured to produce a desired glycoprotein product. In choosing a host cell for the production of the glycoprotein within the context of the present invention, it is important to recognize that different host cells have characteristic and specific mechanisms for the translational and post-translational processing and modification (e.g., glycosylation, cleavage) of the proteins expressed. Appropriate cell lines should be chosen to ensure that the desired post-translational modifications are possible. Alternatively, host cells can be modified to express a desired gene product required for the specific post-translational modification.

In particular, the mammalian cells that express the desired glycoprotein should express or be manipulated to express the particular enzymes such that under suitable conditions, the appropriate post-translational modification occurs in vivo. The enzymes include those enzymes necessary for the addition and completion of N- and O-linked carbohydrates such as those described in Hubbard and Ivatt, *Ann., Rev. Biochem.,* 50: 555–583 (1981) for N-linked oligosaccharides. The enzymes optionally include oligosaccharyltransferase, alpha-glucosidase I, alpha-glucosidase II, ER alpha(1,2)mannosidase, Golgi alpha-mannodase I, N-acetylyglucosaminyltransferase I, Golgi alpha-mannodase II, N-acetylyglucosaminyltransferase II, alpha(1,6)fucosyltransferase, β(1,4)galactosyltransferase, and an appropriate sialyltransferase.

For culturing the mammalian cells that express the desired glycoprotein and are capable of adding the desired carbohydrates in specific position and linkage, numerous culture conditions can be used, paying particular attention to the host cell being cultured. Suitable culture conditions for mammalian cells are well known in the art (Cleveland et al., *J. Immunol. Methods,* 56: 221–234 (1983)) or can be easily determined by the skilled artisan (see, for example, *Animal Cell Culture: A Practical Aprroach* 2nd Ed, Rickwood, D. and Hames, B. D., eds. (Oxford University Press: New York, 1992)), and vary according to the particular host cell selected.

The mammalian cell culture of the present invention is prepared in a medium suitable for the particular cell being cultured. The nutrient solution may optionally be supplemented with one or more components from any of the following categories:

1) plasma components as defined above and/or growth factors such as, for example, insulin, transferrin, and EGF;
2) salts and buffers such as, for example, sodium chloride, calcium, magnesium, phosphate, and HEPES;
3) nucleosides and bases such as, for example, adenosine, thymidine, and hypoxanthine;
4) protein and tissue hydrolysates;
5) antibiotics such as GENTAMYCIN™ drug; and
6) lipids such as linoleic or other fatty acids and their suitable carriers.

Any other necessary supplements may also be included at appropriate concentrations that would be known to those skilled in the art.

Commercially available media such Ham's F10 (Sigma), Minimal Essential Medium (MEM, Sigma), RPMI-1640 (Sigma), and Dulbecco's Modified Eagle's Medium (DMEM, Sigma) are exemplary nutrient solutions. In addition, any of the media described in Ham and McKeehan, *Meth. Enz.,* 58: 44 (1979); Barnes and Sato, *Anal. Biochem.,* 102: 255 (1980); U.S. Pat. No. 4,767,704; U.S. Pat. No. 4,657,866; U.S. Pat. No. 4,927,762; U.S. Pat. No. 5,122,469 or U.S. Pat. No. 4,560,655; WO 90/03430; and WO 87/00195 may be used as culture media. Any of these media may be supplemented as necessary with the components as mentioned above.

The use of a special medium lacking animal serum (serum-free medium) is preferred to avoid interference or counter-action from components of the serum with one or more of the factors, divalent metal cations, plasma components, or other ingredients employed in accordance with the present invention. Moreover, the concentration of the amine groups should be sufficiently high to keep t-PA in solution as the concentration increases. This can be achieved by using greater than about 1 mM lysine concentrations, by the presence of HEPES, or by the use of sufficiently high ammonium chloride concentrations, although any other amine or ammonium source will do.

If the goal is to produce t-PA in substantially single-chain form, the culture medium (just as the medium used in the subsequent recovery and purification steps) contains a protease inhibitor, such as aprotinin, alpha-1 antitrypsin, alpha-2 macroglobulin, soybean trypsin, etc. Preferably, aprotinin is employed at a concentration of about 5 to 100 KIU/ml, more preferably about 10 KIU/ml in the t-PA production medium.

In a particularly preferred embodiment, the mammalian host cell is a CHO cell, preferably CHO-K1 DUX B11. The necessary nutrients and growth factors for the medium, including their concentrations, for a particular cell line, are determined empirically without undue experimentation as described, for example, in *Mammalian Cell Culture,* Mather, ed. (Plenum Press: NY, 1984) and by Barnes and Sato, *Cell,* 22: 649 (1980). A suitable medium contains a basal medium component such as a DMEM/HAM F-12-based formulation (for composition of DMEM and HAM F12 media and especially serum-free media, see culture media formulations in American Type Culture Collection Catalogue of Cell Lines and Hybridomas, Sixth Edition, 1988, pages 346–349), with modified concentrations of some components such as amino acids, salts, sugar, and vitamins, and optionally containing glycine, hypoxanthine, and thymidine; recombinant human insulin, hydrolyzed peptone, such as PRIMATONE HS™ or PRIMATONE RL™ (Sheffield, England), or the equivalent; a cell protective agent, such as PLURONIC F68™ or the equivalent pluronic polyol; GENTAMYCIN™; and trace elements. The formulations of medium as described in U.S. Pat. No. 5,122,469, characterized by the presence of high levels of certain amino acids, as well as PS-20 as described below, are particularly appropriate.

The glycoproteins of the present invention may be produced by growing cells which express the desired glycoprotein under a variety of cell culture conditions. For instance, cell culture procedures for the large- or small-scale production of glycoproteins are potentially useful within the context of the present invention. Procedures including, but not limited to, a fluidized bed bioreactor, hollow fiber bioreactor, roller bottle culture, or stirred tank bioreactor system may be used, in the later two systems, with or without microcarriers, and operated alternatively in a batch, fed-batch, or continuous mode.

In a preferred embodiment the cell culture of the present invention is performed in a stirred tank bioreactor system and a fed-batch culture procedure is employed. In the preferred fed-batch culture the mammalian host cells and culture medium are supplied to a culturing vessel initially and additional culture nutrients are fed, continuously or in discrete increments, to the culture during culturing, with or without periodic cell and/or product harvest before termination of culture. The fed-batch culture can include, for example, a semi-continuous fed-batch culture, wherein periodically whole culture (including cells and medium) is removed and replaced by fresh medium Fed-batch culture is distinguished from simple-batch culture in which all components for cell culturing (including the cells and all culture nutrients) are supplied to the culturing vessel at the start of the culturing process. Fed-batch culture can be further distinguished from perfusion culturing insofar as the supernate is not removed from the culturing vessel during the process (in perfusion culturing, the cells are restrained in the culture by, e.g., filtration, encapsulation, anchoring to microcarriers, etc., and the culture medium is continuously or intermittently introduced and removed from the culturing vessel).

Further, the cells of the culture may be propagated according to any scheme or routine that may be suitable for the particular host cell and the particular production plan contemplated. Therefore, the present invention contemplates a single-step or multiple-step culture procedure. In a single-step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

According to a preferred aspect of the invention, fed-batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($DO_2$), and the like, are those used with the particular host and will be apparent to the ordinarily-skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 40° C. and preferably about 37° C. and a suitable $DO_2$ is between 5–90% of air saturation.

At a particular stage the cells may be used to inoculate a production phase or step of the cell culture. Alternatively, as described above the production phase or step may be continuous with the inoculation or growth phase or step.

According to the present invention, the cell-culture environment during the production phase of the cell culture is controlled. In a preferred aspect, the production phase of the cell culture process is preceded by a transition phase of the cell culture in which parameters for the production phase of the cell culture are engaged.

T-PA production in mammalian, e.g., CHO, cells typically employs a semi-continuous process whereby cells are culture in a "seed-train" for various periods of time and are periodically transferred to inoculum fermentors to initiate the cell-amplification process en route to t-PA production at larger scale. Thus, cells used for rt-PA production are in culture for various periods of time up to a maximum predefined cell age. The parameters of the cell culture process, such as seed density, pH, $DO_2$ and temperature during culture, duration of the production culture, operating conditions of harvest, etc. are a function of the particular cell line and culture medium used, and can be determined empirically, without undue experimentation.

Recovery of the Glycoprotein from the Cell Culture

Following the polypeptide production phase, the glycoprotein of interest is recovered from the culture medium using techniques which are well established in the art. The glycoprotein of interest preferably is recovered from the culture medium as a secreted polypeptide, although it also may be recovered from host cell lysates.

As a first step, the culture medium or lysate is centrifuged to remove particulate cell debris. The glycoprotein thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX G-75™; and protein A SEPHAROSE™ columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the glycoprotein of interest may require modification to account for changes in the character of the glycoprotein upon expression in recombinant cell culture.

Also of utility within the context of the present invention are purification techniques and processes that select for the carbohydrates of the invention. Such techniques include, for example, ion-exchange soft gel chromatography or HPLC using cation- or anion-exchange resins, wherein the more acidic or more basic fraction is collected, depending on which carbohydrate is being selected for.

In a preferred embodiment, CHO cells capable of producing ht-PA are grown as a suspension in a CHO medium to a predetermined cell density. The cell suspension may be concentrated by cross-flow filtration. Active ht-PA is produced subsequently by the CHO cells suspended in the serum-free expression medium. The ht-PA thus produced is secreted by the CHO cells into the expression medium and may be separated from it by standard techniques.

Several techniques may be used for recovery of the t-PA. For example, at the end of the culture, tangential flow filtration, including high-pressure-tangential flow filtration, can be used to remove the medium containing t-PA from the cells.

The cell culture supernatants may concentrated, diafiltered, and loaded onto an affinity column capable of specific binding of t-PA, typically a lysine affinity column. Under the chromatography conditions employed, t-PA adheres selectively to the affinity column from which it can be recovered and subjected to further purification.

In the diafiltration step, the supernatant of the cell culture on a dialysis membrane may be diafiltered with a dialysis buffer comprising propylene glycol, the solution obtained by diafiltration may be loaded on an affinity column capable of selective binding of t-PA, and t-PA may be eluted from the affinity column with a buffer at a pH of about 5.0 to about 9.0. The affinity column preferably is a lysine affinity column, which is preferably eluted at a pH of about 5.0 to about 8.5, more preferably from about 6.0 to about 8.5. Lysine affinity columns are well known in the art and are commercially available. Suitable columns include Lysine CPG™ (Bioprocessing), ECH Lysine CL™ (Pharmacia), and Lysine Hyper D™ (Biosepra). The gel is preferably equilibrated with a 50 mM $Na_2HPO_4$ or $K_2HPO_4$ solution (pH 7.5) prior to loading of the t-PA solution. The elution buffer typically contains 200 mM arginine, and 50 mM $Na_2HPO_4$ or $K_2HPO_4$ (pH 7.5). Preferably, the elution buffer additionally contains propylene glycol in a concentration of about 2.5 to about 20%.

After the foregoing recovery/initial purification steps, the feed stream containing 0.5 to 3.0 mg/ml t-PA simultaneously generally contains about 0.05 to 5 ng/ml of DNA as determined by a DNA dot blot assay using $^{32}$P-labeled DNA derived from the same cell line, resulting in a calculated clearance of approximately $2 \times 10^4$-fold (depending on the source of the lysine resin and on the wash conditions used). To further reduce the level of DNA in the product to less than one picogram per human dose, a specific ion-exchange step may be incorporated into the purification procedure, using commercially available ion-exchange columns, such as a DE-52™ column (Whatman), or DEAE-SEPHAROSE FAST FLOW™ column (Pharmacia).

The purification protocol further includes additional steps that inactivate and/or remove retroviruses that might potentially be present in the cell culture fluid of continuous mammalian cell lines. A significant number of viral clearance steps are available, including additional ultrafiltration/diafiltration steps, treatment with chaotropes such as urea or guanidine, pH extremes, detergents, heat, chemical derivatization, such as formaldehyde, proteases, conventional separation, such as ion-exchange or size exclusion chromatography, organic solvents, etc. The particular step(s) chosen for viral removal is/are not critical aspect(s) of the present invention, and need to meet the following criteria for t-PA: 1. t-PA must be stable under the treatment conditions while the target virus must be sensitive to the treatment, and 2. the "window of clearance" must be maximum. The "window of clearance" is defined for this purpose as the ratio of initial virus titer (spike) in the process fluid prior to the treatment to virus titer after the treatment of the process fluid.

The recombinant human t-PA recovered and purified following the foregoing protocol typically is at least about 97–99.9% pure (depending on the lysine resin). If necessary, further purification can be achieved by additional steps, such as cation-exchange chromatography. Accordingly, the product is suitable for therapeutic applications. Various variants of native human t-PA can be purified by essentially the same procedure, and other glycoproteins may be purified by procedures used for their wild-type counterparts, using procedures well-known in the art.

The present invention is further illustrated by the following, non-limiting examples. It is noted that the method of the present invention is equally applicable to the production of other glycoproteins having more than one glycoform in mammalian cell cultures, and the modifications that might become necessary in the course of the adaptation of the exemplified method to the production of different glycoproteins are well within the skill of an ordinary artisan.

EXAMPLE 1

Temperature Shift in the Production of rht-PA

Materials and Methods

CHO cells: The CHO cell line used as the mammalian host cell line was derived from CHO-K1 (ATCC No. CCL61 CHO-K1), and is a CHO-K1 mutant dihydrofolate reductase (DHFR$^-$)-deficient cell line named CHO-K1 DUX-B11 (DHFR$^-$) (obtained from Dr. L. Chasin of Columbia University; Simonsen and Levinson, supra; Urlaub and Chasin, supra).

PS-20 basal medium: The components of this medium are listed in Table 1 below.

TABLE 1

| Component | Concentration (mg/l) |
| --- | --- |
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Linoleic acid | 0.294 |
| Lipoic acid (DL thioctic acid) | 0.735 |
| Putrescine, dihydrochloride | 0.5635 |
| Sodium pyruvate | 385.0 |
| Alanine | 31.15 |
| Arginine, monohydrochloride | 780.5 |
| Asparagine, monohydrate | 52.53 |
| Aspartic acid | 46.55 |
| Cysteine, monohydrochloride, monohydrate | 122.92 |
| Cystine, dihydrochloride | 31.285 |

TABLE 1-continued

| Component | Concentration (mg/l) |
| --- | --- |
| Glutamic acid | 51.45 |
| Glutamine | 1606.0 |
| Histidine, monohydrochloride, monohydrate | 94.36 |
| Isoleucine | 66.29 |
| Leucine | 98.35 |
| Lysine, monohydrochloride | 200.75 |
| Methionine | 30.68 |
| Phenylalanine | 50.36 |
| Proline | 120.75 |
| Serine | 57.75 |
| Threonine | 89.15 |
| Tryptophan | 15.14 |
| Tyrosine, disodium salt, dihydrate | 79.125 |
| Valine | 87.95 |
| Biotin | 0.0256 |
| D-Calcium pantothenate | 3.68 |
| Choline chloride | 50.86 |
| Cyanocobalamin (B12) | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |
| Glucose | 4301.0 |
| Sodium bicarbonate | 2440.0 |
| Sodium chloride | 5900.0 |
| Pluronic F-68 Prill | 1000.0 |
| HEPES | 2383.0 |
| Phenol Red | 8.10 |

For convenience, the solid ingredients of the medium may be combined together with the amino acids, and this mixture may be stored as a single unit.

Type I/Type II t-PA assay:
1. Thaw cell culture supernatant sample (If whole broth, spin out cells in centrifuge.)
2. Add 2 μl freshly thawed plasminogen to 400 μl of sample.
3. Incubate at 37° C. for 60 minutes.
4. Add 20 μl freshly-thawed 1 M DTT and 400 μl 8 M guanidine-HCl/50 mM TRIS/3.2 mM EDTA solution.
5. Incubate at 37° C. for 15 minutes.
6. Transfer to vial and load 250 μl for assay on HP 1090™ HPLC using the following conditions:
   ZORBAX™ C8 column at 40° C.;
   Monitoring of eluents by fluorescence (excitation at 275 nm, emission at 340 nm);
   Running each sample with the following 70-minute method where eluent A is 0.1% trifluoroacetic acid (TFA) in water and eluent B is 0.1% TFA in acetonitrile:
   0 to 5 min.—75% A (and 25% B)
   5 to 35 min.—a linear gradient from 75% A to 60% A
   35.1 to 45 min.—0% A
   45 min. to 70 min.—75% A to re-equilibrate the column
   Type I/Type II fragments elute after approximately 25 minutes, and peak areas are integrated to determine relative quantities.

Protocol

Recombinant ht-PA-producing CHO cells were carried in spinner flasks passaged every 3 or 4 days (at a density of 0.1% packed cell volume (PCV)) in selective medium (PS-20 basal medium supplemented with 500 mM methotrexate, 10 mg/L recombinant human insulin (rh-insulin), 0.1 ml/L trace elements, and 0.05 ml/L lipid-ethanol). Sufficient culture was removed to seed 15 ml of medium at 0.2% PCV, and placed in a 50 ml sterile Falcon tube. The culture was centrifuged for 10 minutes at 700–1000 rpm and the supernatant was poured off. Upon addition of 15 ml of fresh selective medium, the culture was agitated gently to resuspend cells. Five ml of culture was placed in three T-25 flasks (25 cm$^2$ T-flasks). The caps were left loosened to allow equilibration with incubator atmosphere and the flasks were placed in a 33° C. or 31° C. incubator with 5% carbon dioxide. After 5 to 8 days of incubation, the cells were counted using a hemacytometer and/or by checking packed cell volume, and viability was checked using trypan blue. The culture was removed from the flasks, centrifuged for 10 minutes at 2000–2200 rpm, and the supernatant was assayed for rht-PA glycosylation. Alternatively to the T-25 flasks, the cells were cultured using 60-mm cell culture plates in triplicates.

Supernatants were frozen at −20° C. or −70° C. until the Type I/II t-PA analysis took place.

For spinner experiments, the foregoing protocol was used, except the cells were passaged into 200 ml of fresh medium (with initial PCV of 0.1%), in a 250-ml spinner flask. The caps were closed tightly on the flask, which was then placed in the 33° C. or 31° C. incubator on a magnetic stir plate at 60 rpm.

The mini-fermentor experiments were performed under standard t-PA production conditions in fed-batch mode as noted herein in 5-liter stirred tank bioreactors (Applikon, Foster City, Calif.). The temperature was shifted to 33° C. or 31° C. on day 2 of the production phase.

For control experiments, the foregoing experiments were followed, except that incubation took place at 37° C. Further, experiments were performed as above in 12-K fermentors over the course of 200 hours and the percentage of Type I t-PA was assessed.

For the experiments herein and below, culture conditions were usually changed on day 1 (e.g., addition of different media components) and day 2 (e.g., temperature shift).

Results t-PA site occupancy at Asn-184 was found to be relatively consistent across a variety of scales (T-flask, spinner, and 80-L, 400-L, 2000-L, and 12,000-L fermentors) (FIG. 2) and from run to run in production. The factors that can affect site occupancy include those factors affecting oligosaccharide-dolichol availability (dolichol phosphate, lipids, and hormones), factors affecting protein translation elongation rate (e.g., cycloheximide), factors affecting oligosaccharyl-transferase activity or protein folding rate (e.g., dithiothreitol), and factors acting through unknown mechanisms, such as time in culture. Illustrating the latter-most phenomenon, FIG. 3 shows graphs of the percentage of Type I human t-PA in cell cultures of CHO cells at 37° C. as a function of 12K-fermentation run time, with each graph line representing a different run. These results show that site-occupancy increases over the course of a batch culture (over culture length).

FIG. 4 shows that reducing temperature increases t-PA site occupancy. Specifically, FIG. 4A shows the results of laboratory-scale experiments performed for 5–7 days (T-flasks and spinner flasks). In the control experiments, where in the production phase the temperature remained at 37° C., the product contained about 38% Type I t-PA. In contrast, in the experiments where in the production phase the temperature was lowered to 33° C., the t-PA product obtained contained about 43–46% Type I t-PA. FIG. 4B shows the results of bioreactor experiments, indicating that the lower temperature similarly yields a higher percentage of Type I t-PA.

EXAMPLE 2

Butyrate Addition in the Production of rht-PA

Materials and Methods

The quantity of cells needed for a 0.2% packed cell volume seed density was centrifuged at approximately 700×g for 10 minutes, and resuspended in 25 cm² T-flasks in the appropriate fresh medium for each test case. The T-flasks were set up in triplicate with 5 mL in each flask and incubated for 3 to 4 days at 37° C. and 95% air 5% $CO_2$. Sodium butyrate was added to a concentration of 0.375 mM, 0.75 mM, or 1.5 mM at the time of inoculation for the 25 cm² T-flasks. Cells were also cultured in spinner flasks at volumes of 100 ml with similar butyrate concentrations to the T-flask cases. For fermentor experiments, butyrate was added on the second day of the experiments. T-flask cultures were also carried out at 33° C. and 37° C. with no butyrate additions. The data shown for the T-flask cultures at 33° C. are from two triplicate experiments (n=6). T-PA site-occupancy was analyzed using the method of Example 1.

Results

FIG. 5 shows that the presence of sodium butyrate at concentrations of 0.375 to 1.5 mM at the time of inoculation increased t-PA site-occupancy in the T-flasks at 37° C. The same increased effect was observed for the spinner flask and fermentor experiments.

FIG. 6 shows that for the 60-mm culture plate experiments, temperature shifts to 33° C. and 31° C. had the largest effect and increased t-PA site-occupancy gradually up to 6%. 0.75 mM butyrate increased the Type I content slightly (about 1%) compared to no butyrate (FIG. 6). In contrast, a further increase of the butyrate concentration (1.5 mM) lowered site-occupancy at 37° C. and 33° C., but increased it at 31° C. (FIG. 6).

FIG. 7 shows the effect of temperature and butyrate on t-PA site-occupancy in 5-liter bioreactors. The Type I content was analyzed on days 5–7. Decreasing temperature from 37° C. to 33° C. increased t-PA site occupancy. However, increasing the butyrate concentration from 0.75 to 1.5 mM decreased the Type I content at both temperatures. This confirms the data obtained in 60-mm plate experiments (see FIG. 6).

EXAMPLE 3

Cell-cycle Inhibitor Addition in the Production of rht-PA

Introduction

Temperature reduction, culture length, and butyrate addition were found to increase the glycosylation of t-PA at the Asn-184 site, as noted in Examples 1 and 2. All of these factors correspond with decreased cell growth rate, leading to the hypothesis that glycosylation and site-occupancy are cell-cycle dependent. This hypothesis was tested by performing two additional experiments reflected in this example using cell-cycle inhibitors (quinidine and thymidine).

Materials and Methods

Cells were cultured as for the sodium butyrate experiment described in Example 2. Thymidine was dissolved in water and sterile filtered for a 33–36× stock solution. Quinidine was made up in dimethyl sulfoxide (DMSO) and filtered to make a 1000–1800× stock. Thymidine and quinidine were added to the cultures at the time of inoculation to final concentrations of 250 µg/mL and 90 µM, respectively. T-PA site-occupancy was analyzed using the method of Example 1.

Results

The cell cycle analysis for the control, the quinidine, and the thymidine is shown in Table 2, as determined by model F_AN1_T3.MOD.

TABLE 2

| | Cell-Cycle Analysis | | |
|---|---|---|---|
| Analysis | Cell Cycle Control | Quinidine | Thymidine |
| G0/G1 | 53.91% at 84.70 | 67.34% at 84.65 | 32.58% at 84.60 |
| G2-M | 11.72% at 165.58 | 8.55% at 165.45 | 10.09% at 165.36 |
| S | 34.37% | 24.11% | 57.33% |
| G2/G1 | 1.95 | 1.95 | 1.95 |
| % CV | 1.97 | 1.79 | 1.99 |

FIG. 8 shows that site occupancy and cell-cycle position vary similarly over time in a culture. FIG. 9 shows that quinidine blocks the cells in the G1/G1 phase (with 67% in the G0/G1 phase) and results in increased site occupancy as compared to the control with no cell-cycle inhibitor (54% in the G1/G1 phase), and thymidine causes the cells to accumulate in the S/G2 phases (with 33% in the G0/G1 phase) and results in decreased site occupancy as compared to the control. These results confirmed that factors that increase the proportion of cells in the G0/G1 phase increase site occupancy.

EXAMPLE 4

Divalent Metal Cation, Nucleotide Sugar Precursor, and Hormone Addition in the Production of rht-PA Materials and Methods All experiments were done in 60-mm culture dishes using the procedure described in Example 1 except that a Mn salt, Fe salt, nucleotide sugar precursor, or hormone was added to the growth medium during the growth phase, with Mn or Fe salt or nucleotide sugar precursor added on day 1. All plates were inoculated at a seeding density of 0.1% PCV and a working volume of 6–8 ml. All cases were done in triplicates. Plates were incubated at 37° C. in $CO_2$ incubators.

The amounts of $MnCl_2$ or ferric citrate in the growth medium during the growth phase were increased. For $MnCl_2$ 3 nM was the control, with increasing amounts of $MnCl_2$ at concentrations of 10 nM, 100 nM, 1 µM, 10 µM, and 100 µM. For ferric citrate, the control was no salt, with increasing amounts at 10, 50, and 100 µM. The amounts of uridine, adenosine, and guanosine were 0.5 mM each and the amount of mannose was 5 g/l (guanosine and mannose were combined), and -GHT is selective medium minus glycine, hypoxanthine and thymidine.

The amounts of tri-iodothyronine and thyroxine employed in the culture medium were increased relative to a control with no hormone, with amounts of 1 nM, 10 nM, or 100 nM tri-iodothyronine, or 1 nM, 10 nM, or 100 nM thyroxine.

T-PA site-occupancy was analyzed on days 4–6 (manganese, iron, or nucleotide sugar precursor experiment) or on day 7 (hormones) using the method described in Example 1.

Results

The effect of increasing manganese concentration on t-PA site-occupancy (triplicate runs) is shown in FIGS. 10A and 10B. Supplementing the medium with additional manganese over the 3 nM control value significantly increased the t-PA Type I content (improved site-occupancy) about 2.5%. A positive titration effect was observed between 3 nM and 100 nM. No further improvement occurred when increasing the concentration up to 100 µM, which is still an effective concentration.

Oligosaccharyltransferase requires $Mn^{2+}$ ions for maximal activity, but other divalent metal cations with an octahedral coordination geometry, including Mg, Ca, and Fe, will support transfer, albeit at reduced rates (Hendrickson and Imperiali, suprs, and Kaufman et al., supra). Hence, the effect of $Fe^{2+}$ on t-PA site-occupancy was investigated. As is evident from FIG. 11, the addition of 10–100 µM $Fe^{2+}$ (ferric citrate) increased t-PA site occupancy gradually up to about 4%.

Increasing the availability of nucleotide sugar precursors (e.g., nucleosides, mannose, glycine, thymidine, or hypoxanthine) did not improve site-occupancy. Moreover, the addition of uridine and guanosine decreased t-PA site-occupancy about 2% (see FIG. 12).

The effect of thyroid hormones (thyroxine and triiodothyronine) on t-PA site-occupancy is shown in FIGS. 13A and 13B. These hormones increased site-occupancy about 2%, and it is expected that other plasma components as defined above would similarly have such an effect.

In conclusion, several culture conditions that affect t-PA N-glycosylation site-occupancy have been identified. These factors are potentially useful to further improve product consistency. T-PA site occupancy at Asn-184 is relatively consistent across a variety of conditions, including a variety of scales (T-flask, spinner, 80-liter, 400-liter, 2000-liter, and 12,000-liter), and from run to run in production. Factors that increase the proportion of cells in the G0/G1 phase, such as temperature, butyrate, and cell-cycle inhibitors, increase site occupancy, as do increased amounts of certain divalent metal cations and/or plasma components preferably present during the whole cultivation time.

The entire disclosures of all citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made without diverting from the overall concept of the invention. All such modifications are intended to be within the scope of the present invention.

What is claimed is:

1. A process for producing a human glycoprotein having multiple glycoforms, comprising culturing Chinese hamster ovary cells expressing nucleic acid encoding said glycoprotein in a serum-free medium in a production phase at a temperature of about 30° C. to 35° C. and in the presence of about 0 to 2 mM of a butyrate salt, wherein the process produces an increased percentage of glycoprotein molecules having one glycoform relative to an identical process performed at 37° C. in the absence of butyrate.

* * * * *